(12) United States Patent
De Backer

(10) Patent No.: US 7,540,843 B2
(45) Date of Patent: Jun. 2, 2009

(54) DIAGNOSTICS AND TREATMENT OF SLEEP APNEA

(75) Inventor: Wilfried De Backer, Edegem (BE)

(73) Assignee: Universiteit Antwerpen, Antwerpen (BE)

(*) Notice: Subject to any disclaimer, the term of this patent is extended or adjusted under 35 U.S.C. 154(b) by 0 days.

(21) Appl. No.: 11/576,589

(22) PCT Filed: Oct. 5, 2005

(86) PCT No.: PCT/EP2005/010730

§ 371 (c)(1),
(2), (4) Date: Apr. 3, 2007

(87) PCT Pub. No.: WO2006/037627

PCT Pub. Date: Apr. 13, 2006

(65) Prior Publication Data

US 2007/0255161 A1    Nov. 1, 2007

(30) Foreign Application Priority Data

Oct. 5, 2004    (EP) ............... PCT/EP2004/011108

(51) Int. Cl.
*A61B 5/08* (2006.01)
*A61B 5/05* (2006.01)
*A61B 8/00* (2006.01)

(52) U.S. Cl. ............... 600/538; 600/533; 600/407; 600/410; 600/437; 600/411; 600/529

(58) Field of Classification Search ......... 600/529–543, 600/300, 301, 484, 407, 410, 411, 437, 587, 600/593; 128/920–925, 204.23
See application file for complete search history.

(56) References Cited

U.S. PATENT DOCUMENTS

| | | | | |
|---|---|---|---|---|
| 4,326,416 | A * | 4/1982 | Fredberg | 600/533 |
| 5,445,144 | A * | 8/1995 | Wodicka et al. | 128/207.14 |
| 5,729,694 | A * | 3/1998 | Holzrichter et al. | 705/17 |
| 5,782,762 | A * | 7/1998 | Vining | 600/407 |
| 5,882,314 | A * | 3/1999 | Fredberg et al. | 600/529 |
| 5,931,160 | A * | 8/1999 | Gilmore et al. | 128/204.21 |
| 5,971,934 | A * | 10/1999 | Scherer et al. | 600/526 |
| 6,083,162 | A * | 7/2000 | Vining | 600/407 |
| 6,183,423 | B1 * | 2/2001 | Gaumond et al. | 600/529 |
| 6,272,366 | B1 * | 8/2001 | Vining | 600/407 |
| 6,379,311 | B1 * | 4/2002 | Gaumond et al. | 600/529 |
| 6,440,083 | B1 * | 8/2002 | Fredberg et al. | 600/533 |
| 6,694,163 | B1 * | 2/2004 | Vining | 600/407 |

(Continued)

*Primary Examiner*—Charles A Marmor, II
*Assistant Examiner*—Navin Natnithithadha
(74) *Attorney, Agent, or Firm*—Knobbe, Martens, Olson & Bear, LLP

(57) ABSTRACT

Methods of diagnosis and treatment of sleep apnea by taking measurements from a subject suffering from sleep apnea are disclosed. The methods include modelling the air flow through the upper airway of a subject suffering from sleep apnea.

13 Claims, 26 Drawing Sheets

U.S. PATENT DOCUMENTS

| | | | |
|---|---|---|---|
| 6,901,277 B2 * | 5/2005 | Kaufman et al. | 600/407 |
| 6,909,913 B2 * | 6/2005 | Vining | 600/407 |
| 7,017,574 B2 * | 3/2006 | Biondi et al. | 128/204.21 |
| 7,094,206 B2 * | 8/2006 | Hoffman | 600/529 |
| 7,334,578 B2 * | 2/2008 | Biondi et al. | 128/204.23 |
| 7,421,296 B1 * | 9/2008 | Benser et al. | 607/42 |
| 7,427,269 B2 * | 9/2008 | George et al. | 600/532 |
| 7,435,226 B2 * | 10/2008 | Suarez | 600/536 |
| 2003/0100843 A1 * | 5/2003 | Hoffman | 600/538 |
| 2004/0249301 A1 * | 12/2004 | Stenqvist | 600/538 |
| 2005/0165457 A1 * | 7/2005 | Benser et al. | 607/42 |
| 2006/0241509 A1 * | 10/2006 | Badr | 600/533 |
| 2007/0225587 A1 * | 9/2007 | Burnell et al. | 600/407 |

* cited by examiner (A)

(B)

(C)

(A)

(B)

(C)

DIAGNOSTICS AND TREATMENT OF SLEEP APNEA

RELATED APPLICATIONS

This application is the U.S. National Phase under 35 U.S.C. §371 of International Application PCT/EP2005/010730, filed Oct. 5, 2005, which claims priority to PCT/EP2004/01108, filed Oct. 5, 2004.

The present invention relates to diagnosis and treatment of sleep apnea by using measurements individually taken of a subject suffering from sleep apnea to treat the condition.

Obstructive sleep apnea (OSA) is a frequently occurring condition that affects at least 4% of males and 2% of females (1). Symptoms of OSA include daytime sleepiness and fatigue, loss of concentration and insufficient recuperation during sleep. OSA is characterised by repeated obstruction, collapse of the upper airway during sleep (3,4). The apneas lead to oxygen desaturation and repeated awakenings.

Sleep apnea is clinically diagnosed by taking measurements during the sleep of a patient. These measurements record the flow and the pressure at the different locations continuously throughout the night. Several treatments, such as nasal Continuous Positive Airway Pressure (nCPAP) (2), bilevel positive airway pressure (BiPAP), auto Continuous Positive Airway Pressure (autoCPAP), dental appliances and surgical therapy, already exist.

Nasal Continuous Positive Airway Pressure (nCPAP) increases the intraluminal pressure in the airway and thereby prevents the collapse of the upper airway. Many invasive techniques have been developed, which intervene only in the upper airway, for example, dental appliances or surgery. Dental devices include a mandibular advancement device (20). Surgical treatments for OSA alter the upper airway anatomy to eliminate sites of obstruction. Surgical treatments include tracheostomy, uvulopalatopharyngoplasty, laser assisted uvuloplasty, geniohyoid advancement procedure and the maxillomandibular advancement procedure. Surgical treatment can achieve a good rate of success, but there is no means of deciding on most suitable course of therapy.

Deciding on the best treatment or optimizing a treatment necessitates actual implementation of the therapy. Only once implemented can it be discovered whether or not it is effective. Furthermore, once implemented, a treatment has the potential to be optimized. With present methods such optimization is laborious requiring extensive patient/physician time, for example, use of a sleep laboratory.

In view of the prior art, there is a need for optimizing the treatment of sleep apnea, which minimizes the time of the patient and physician. Such need may predict the most appropriate therapy, and/or optimize a chosen therapy.

SUMMARY OF SOME EMBODIMENTS OF THE INVENTION

One embodiment of the present invention is a method for diagnosing and/or determining the treatment of obstructive sleep apnea comprising modeling the air flow through the upper airway of a subject suffering from the same.

One embodiment of the present invention is a method as described above comprising the step of measuring the flow and pressure at the palatopharynx, oropharynx, and/or hypopharynx of said subject during an apnea episode.

One embodiment of the present invention is a method as described above comprising the step of obtaining a three-dimensional image of the upper airway of said subject.

One embodiment of the present invention is a method as described above comprising the step of obtaining a two-dimensional image of the upper airway of said subject, being a sagittal plane along the central axis of the upper airway.

One embodiment of the present invention is a method as described above comprising the step of generating a two dimensional model from said image, being across a sagittal plane along the central axis of the upper airway.

One embodiment of the present invention is a method as described above comprising a use of a CFD code 2 analysis.

One embodiment of the present invention is a method as described above comprising the use of fluid-structure interactions.

One embodiment of the present invention is a method as described above comprising the use of a CFD code 1 analysis.

One embodiment of the present invention is a device for providing positive airway pressure therapy configured with data obtainable from a method as described above.

One embodiment of the present invention is a use of a device for providing positive airway pressure therapy configured with data obtainable from a method as described above for the treatment of obstructive sleep apnea.

One embodiment of the present invention is a mandibular advancement device configured according to data obtainable from a method as described above.

One embodiment of the present invention is a use of a mandibular advancement device for providing positive airway pressure therapy configured with data obtainable from a method as described above, for the treatment of obstructive sleep apnea.

One embodiment of the present invention is a dynamic model obtainable using a method as described above.

DETAILED DESCRIPTION OF THE PRESENT INVENTION

The present invention relates to the use of measurements individually taken of a subject suffering from sleep apnea to treat the condition. Measurements taken of the subject while sleeping, such as the flow and pressure at particular locations in the throat, together with a model of the upper airway, may be used by a technician to diagnose the cause of the apnea.

Figure 1:
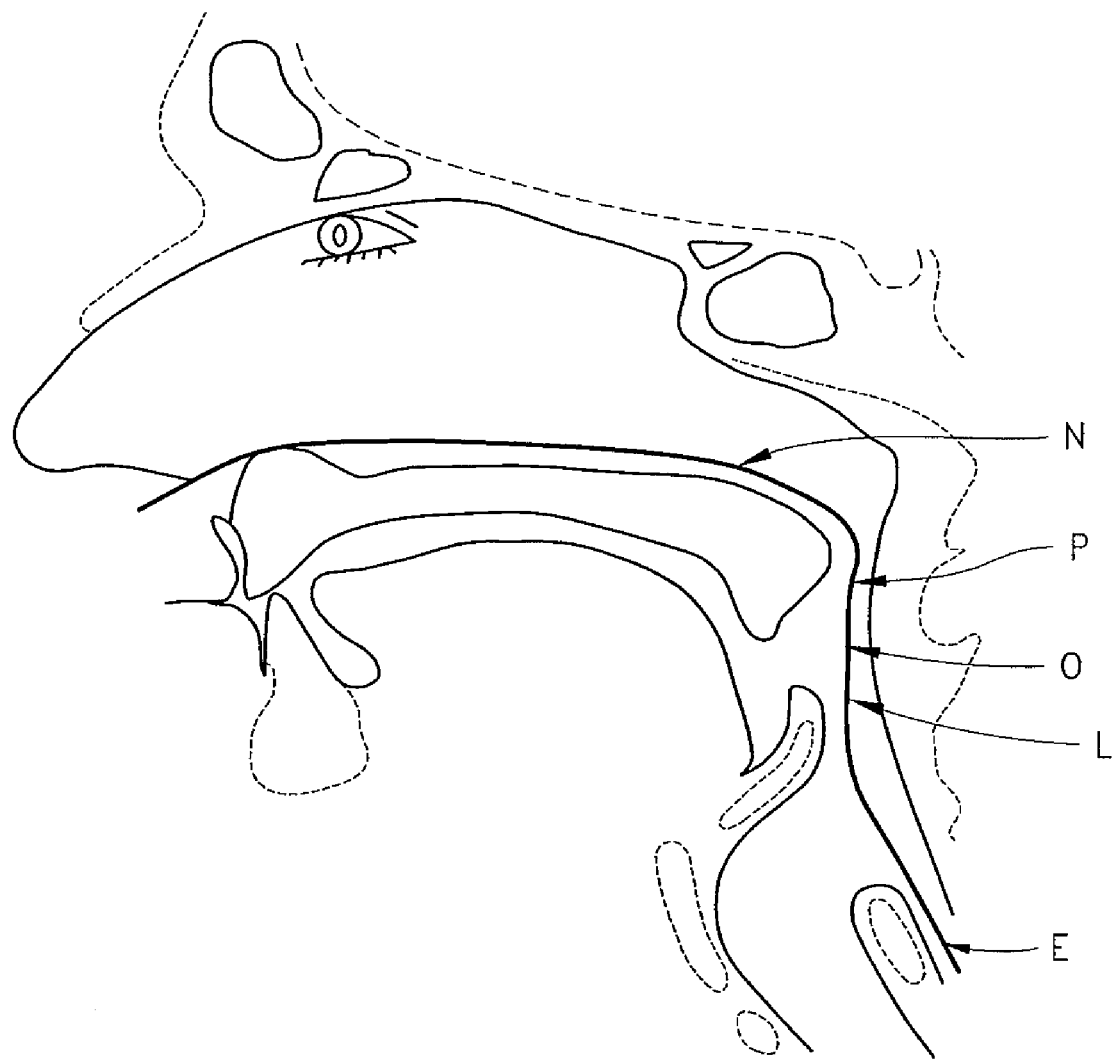
FIG. 1 Drawing of the upper airway showing the nasopharynx (N), palatopharynx (P), oropharynx (O), hypopharynx (L) and oesophagus (E).

According to one aspect of the invention, measurements are made whilst sleeping. During an apnea pressures at the palatopharynx (P), oropharynx (O), and/or hypopharynx (L) of a subject (FIG. 1). are measured.

Such measurements may be made using any method of the art. Air pressures may be measured by inserting a catheter containing four balloons in the upper airway. The result of these measurements is a graph depicting the pressures at P, O and L during a breathing cycle. From such a graph, it is possible to determine several parameters including approximately the location at which the apnea occurs.

Flow is measured using a pneumotachograph which allows quantitative well calibrated measurements.

According to one aspect of the invention, a model of the upper airway is generated using any method of the art. Such methods include magnetic resonance imaging, positron emission tomography and computer tomography imaging to name a few. Such model may be generated of the subject while he is sleeping and breathing normally, during apnea, or preferably while the subject is awake and breathing normally. The method to generate the model may provide a three-dimensional (3D) image or a two (2D) dimensional image.

Figure 10:
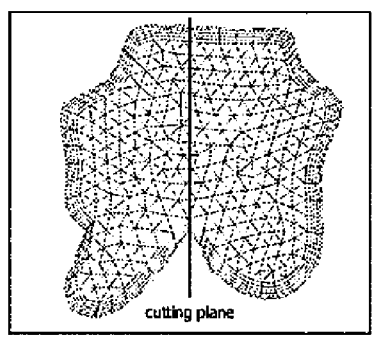
FIG. 10 An example of cutting plane along the sagittal axis.

A two dimensional image is preferably along the longitudinal axis of the upper airway, in the sagittal plane. Preferably, the plane cuts through a central axis of the upper airway or close thereto (FIG. 10). According to an embodiment of the invention, the plane joins the midpoint of the inlet with the midpoint of the outlet. According to an embodiment of the invention, the plane intersects the midpoint of the upper airway along its longitudinal axis.

The two or three dimensional images are converted into a model. Such model can be any of the art, such as, for example, wire mesh, polygon and cloud point. Such model may comprise a structured boundary layer grid disposed across at least part of the wall of the upper airway model, and an unstructured tetrahedral grid in the middle. Such images are capable of manipulation and processing in a Computer Aided Design (CAD) environment.

Where a three dimensional model has been generated, it is an aspect of the invention that a two dimensional (2D) model is formed therefrom. Such 2D model is formed from a cross-section of the longitudinal axis of the 3D model, across the sagittal plane. Preferably, the plane cuts through a central axis of the upper airway or close thereto. According to an embodiment of the invention, the plane joins the midpoint of the inlet with the midpoint of the outlet. According to an embodiment of the invention, the plane intersects the midpoint of the upper airway along its longitudinal axis.

Using a 2D model in a method according to the invention permits calculation times to be reduced compared with the use of 3D models, hence leading to a faster diagnosis. However, where a 2D model is used in the calculations as described herein, it may be replaced with a 3D model.

According to an aspect of the invention, measurements taken of a subject while sleeping, such as the flow and pressure at particular locations in the throat, together with a model of the upper airway are used to provide information regarding the flow properties during a normal expiration during sleep. Such information enables a technician to determine possible causes of airway collapse. It can be used to predict the outcome of a local intervention. The intervention may be, for example, advancing the mandibula to increase the cross sectional area of upper airway, thereby increasing the pressure at the base of the tongue preventing a collapse from occurring.

According to an embodiment of the invention, the airflow through the upper airway is modeled using the flow and pressure at particular locations in the throat, together with a model of the upper airway. Such a flow model may be a computation fluid dynamic (CFD) model.

According to an aspect of the invention, a flow model is generated by solving the Navier-Stokes equations.

—CFD Analysis Without Fluid Structure Interaction (FSI)—
CFD Code 1

According to an aspect of the invention, an initial, rapidly generated flow model is made in order to provide the technician with information regarding, for example, the speed of flow, pressure and velocity of air at particular moments in time and at particular regions in the upper airway. Such information provides an approximate indication of, for example, the forces involved during expiratory phase. Such information also enables flow properties determined using a 3D model of the upper airway to be compared with flow properties determined using a 2D model. Such comparison confirm the validity of using a 2D model or permits correction if necessary. However, where a 2D model is used in the calculations as described herein, it may be replaced with a 3D model.

According to an aspect of the invention, the flow in a model is unsteady, viscous and incompressible. The mean diameter of the airway is such that flow is turbulent; the Reynolds number, based on the mean diameter of the tube at the time of maximum flow is in the order of 6000, which as indicated in literature (6, 7), leads to a turbulent flow.

According to one aspect of the invention, a turbulence model is used for an initial analysis, for example, the one-equation Spalart-Allmaras model (8). As used herein, the analysis including turbulence is known as "CFD code 1" analysis. It produces a dynamic model of airflow within the upper airway, indicating, for example, pressure, flow and velocity as contours. The application of the CFD code 1 analysis does not require significant computational time and it allows a reasonable comparison with the further modeling routines described herein (e.g. CFD code 2 calculations where the zero-equation mixing length model (9, incorporated herein by reference) is used). Methods of implementing CFD code 1 procedure are well known in the field, for example, from (8) (Fluent) which is incorporated herein by reference.

According to one aspect of the invention, the boundary conditions are set to velocity inlet and pressure outlet in the CFD code 1 procedure, to account for the nasal resistance. See example Examples 6, 7, 8 and 9.

The inventors have found that a flow model generated using a CFD code 1 analysis provides a rapid and accurate method of assessing the flow characteristics in the upper airway during expiration.

—CFD Code Using FSI—CFD Code 2

According to an aspect of the invention, a more detailed flow model is generated in order to provide the technician with information regarding, for example, the flow speed, pressure and velocity of air at particular moments and in particular regions in the upper airway and simulate the upper airway collapse in patients suffering from sleep apnea.

According to an aspect of the invention, the flow in a model is unsteady, viscous and incompressible. The turbulence model applied is the zero-equation mixing length model. "CFD code 2" analysis is a Navier-Stokes solver. Such CFD code 2 analysis is known in the art and includes, but is not limited to "Fidap" as is described in reference (9) and incorporated herein by reference. Such flow model provides an indication of the flow, pressure and velocity, optionally together with behaviour of at least part of the wall of the upper airway. The inventors have found that such detailed flow model may be generated using a 2D model of the upper airway, while generating sufficiently detailed and accurate information enabling a technician to deduce the type of airway blockage. The use of a 2D model greatly enhances the speed of calculation compared with a 3D model. However, where a 2D model is used in the calculations as described herein, it may be replaced with a 3D model.

According to one aspect of the invention, a CFD code 2 analysis includes Fluid Structure Interactions (FSI). FSI takes into account the properties of the wall of the airways. For example, the movement of the wall during breathing, and subsequent collapse during an apnea episode can be modeled.

According to an aspect of the invention, the boundary conditions for the flow are based on real data taken from in-patient measurements during sleep studies. The inlet boundary condition may be a velocity inlet boundary condition. The velocity is derived from the flow measurements where the inlet area A and the density may be assumed to be constant. The velocity may then be calculated using equation 1:

$$V = \frac{\dot{m}}{\rho A} \quad \text{(Eq. 1)}$$

The outlet boundary condition is set to pressure outlet. Here the pressure, also based on real data, is described. This pressure increases during expiration to overcome the nasal resistance.

Figure 2:
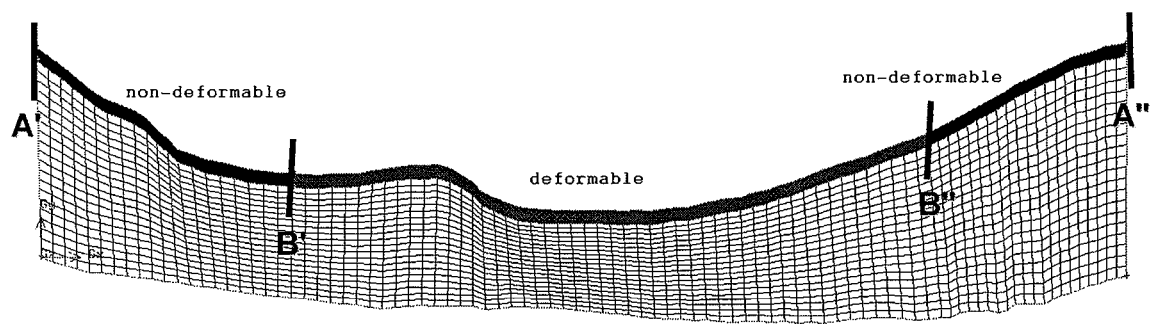
FIG. 2 Drawing indicating the wall boundary (B) conditions—nondeformable at the edges and deformable a central region.

According to another aspect of the invention, boundary conditions imposed on the wall. As with the Starling resistor model (13) a part of the wall is deformable, while the other parts are fixed. FIG. 2 presents the wall boundary conditions. The central zone represents the deformable part of the model while the outer regions show the non-deformable part.

According to another aspect of the invention, the weight of the wall used in the calculation is determined iteratively. According to one aspect it is between 0.5 and 2.5 kg, 1 and 2 kg, 1.5 to 1.75 kg 1.85 and 2.4 kg, or the weight is 1.85 kg, or 2.4 kg.

According to another aspect of the invention, the Young's modulus is taken to be constant during expiration. According to another aspect of the invention, the time function for the muscle relaxation is iteratively determined.

According to one aspect of the invention the effective nCPAP pressure (the pressure applied at the upper airway that prevents collapse) may be based on the data obtained with the invention. Effective pressures calculated with the invention method may be applied with nCPAP, BiPAP or autoCPAP, so optimizing therapy therewith.

One embodiment of the present invention, therefore, is the adjustment of a device for applying positive airway pressure to a subject suffering form sleep apnea using the method of the invention.

One aspect of the invention is a device for applying nCPAP pressure to a subject suffering form sleep apnea, configured using information obtained or obtainable using a method of the invention.

Another embodiment of the present invention is a use of a device for applying positive airway pressure to a subject suffering form sleep apnea in a method of the invention.

Another embodiment of the present invention is a flow model obtained using a method of the present invention.

Another embodiment of the present invention is a use of a flow model obtained according to the invention for determining the best surgical therapy treatment.

Another embodiment of the invention is a mandibular advancement device (MAD) configured using information obtained or obtainable using a method of the invention. In a mandibular advancement device (20) the mandibula is pushed forward with an in-patient apparatus to increase the diameter of the upper airway. Changes in upper airway cross sectional area obtained by the mandibular advancement devices may be put into the model, making a prediction of the tendency to collapse the upper airway wall after the treatment with MAD possible.

EXAMPLES

Example 1

Obtaining Patient Specific Data

The patient under consideration suffers from severe obstructive sleep apnea and has participated in a sleep study. During this study the flow and the pressures are monitored during the night. This patient was chosen for his pronounced form of sleep apnea and for the availability of the clinical data.

Figure 3:
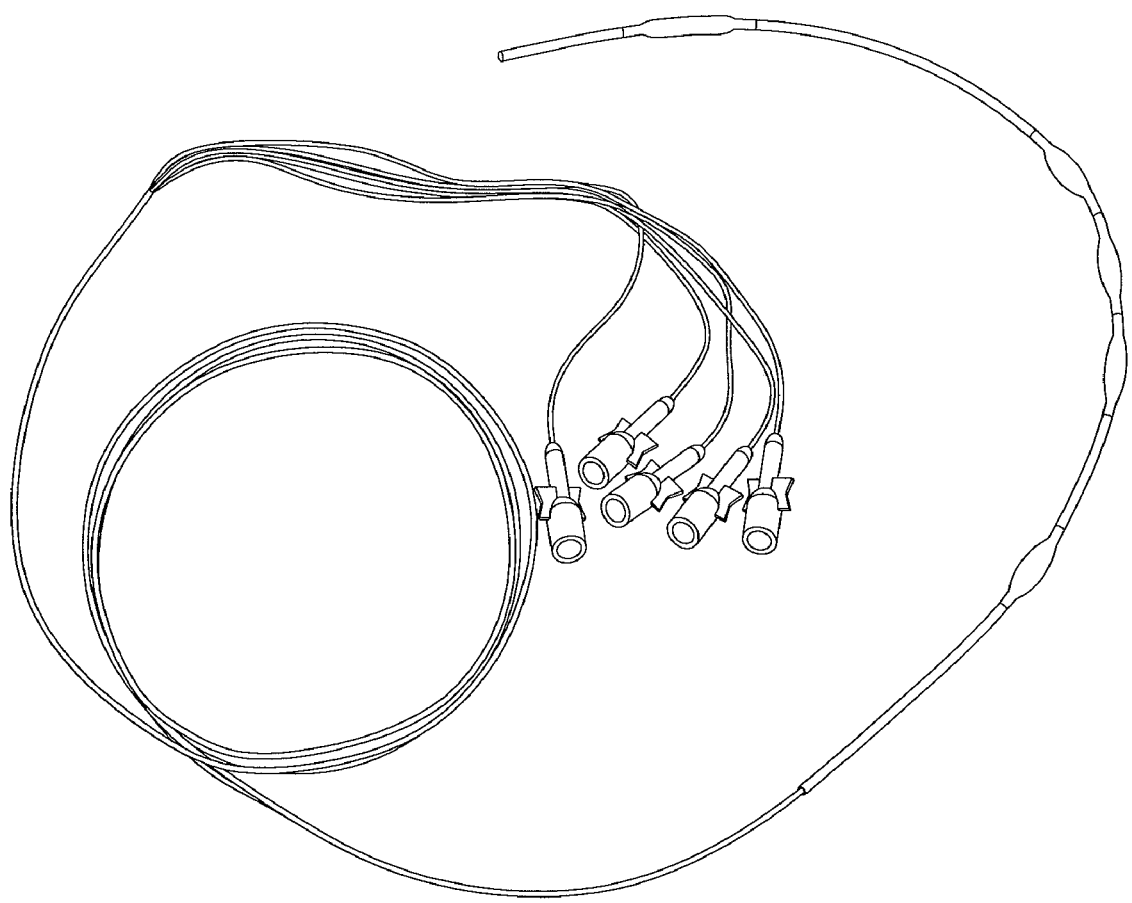
FIG. 3 Catheter used for pressure measurements.

The data of interest for this analysis are the flow and the pressure at the locations P, O and L. The flow is measured using a pneumotacograph, the pressures are measured by inserting a catheter in the upper airway which contains four balloons. The catheter is shown in FIG. 3.

Figure 4:
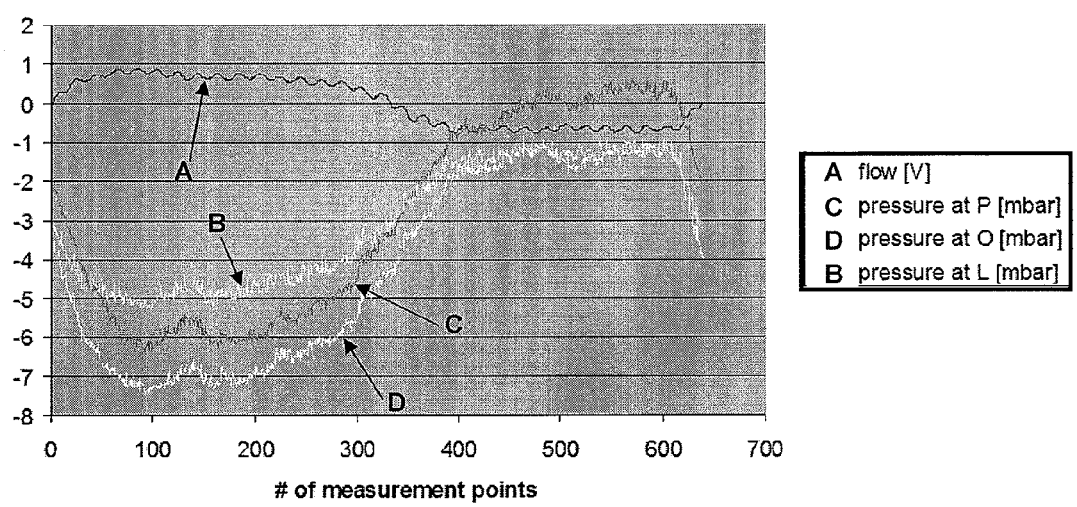
FIG. 4 Measurements during 1 breathing cycle.

FIG. 4 shows one inspiration and expiration measured during the night. It depicts the flow and the pressure at P, O and L.

The oscillations shown in the flow are caused by the application of the Forced Oscillation Technique[5] in order to calculate the impedance of the airway. These oscillations are not of interest for the present analysis and can be ignored.

Figure 5:
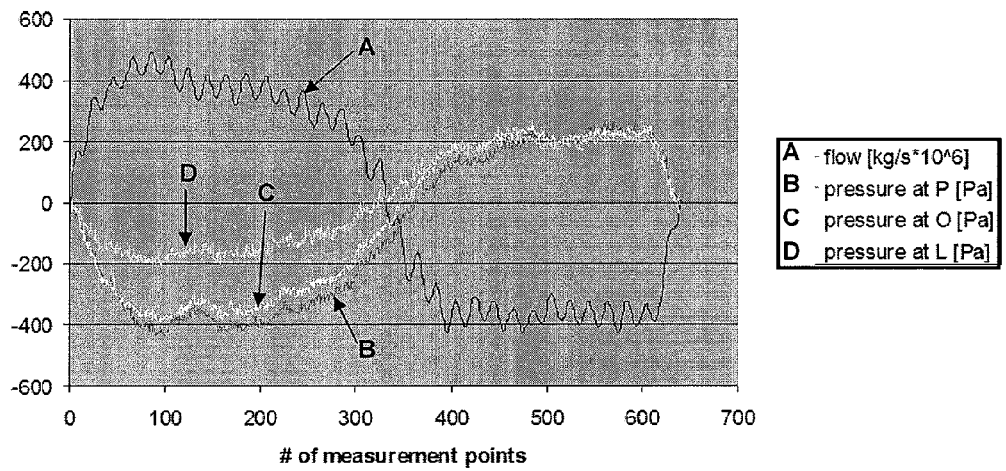
FIG. 5 Measurements during 1 breathing cycle—corrected for errors.

The values for the pressure shown in FIG. 4 are interpreted to account for errors. The catheter used to measure these pressures, shown in FIG. 3, has a limited accuracy due to the narrow tubes. Connecting the tubes to the measurement box induces an error of a few mbar. The standard is to correct for this error by setting the values at the beginning of the expiration equal to zero. FIG. 5 shows corrected values for the pressure in Pa. The flow is converted to kg/s and multiplied by $10^6$. From these corrected values for the pressure two conclusions can be drawn:

1. During expiration the intraluminal airway pressure, $P_{in}$, increases to 200 Pa at maximum flow. This indicates that there is a large amount of 'nasal resistance', which creates the need for a relatively large pressure to induce flow. In order to account for this resistance, the boundary condition at the 'outlet' will be set to a pressure outlet, where this transient pressure can be defined.
2. The correction that is introduced here varies between 200 to 350 Pa. This correction is an order of magnitude larger than the pressure difference observed between the three balloons at a certain time. This indicates that the absolute values for the pressure cannot be used for validation. The variation over time on one location provides a good approximation.

Figure 6:
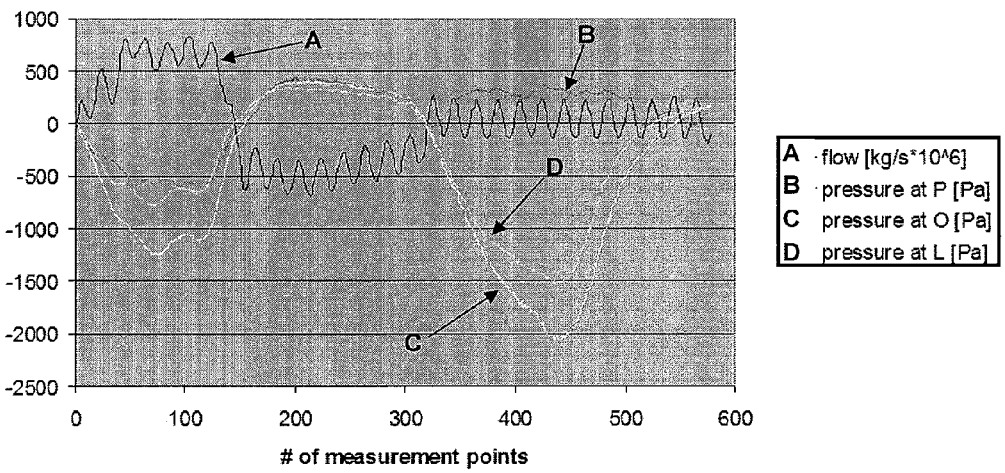
FIG. 6 Measurements before and during apnea.

FIG. 6 shows an example of an expiration that results in an apnea. The data for this specific expiration is used for the model. The values for the pressure have been corrected as described above. This figure clearly demonstrates that the apnea (zero flow) occurs towards the end of the expiration with the collapse between point O and point P. At O and L there is still a variation in pressure due to the drive the patient's reflex to breathe. Collapse of the airway in front of point P causes the signal to remain constant at this location. These pressure measurements can give an indication of the location of the collapse, which is important for validating the model later on. For this specific patient the occurrence of an apnea can be avoided by applying a CPAP pressure of 6 $cm_{H2O}$, which is equivalent to 588 Pa.

Example 2

Construction of 3D Model

Figure 7:
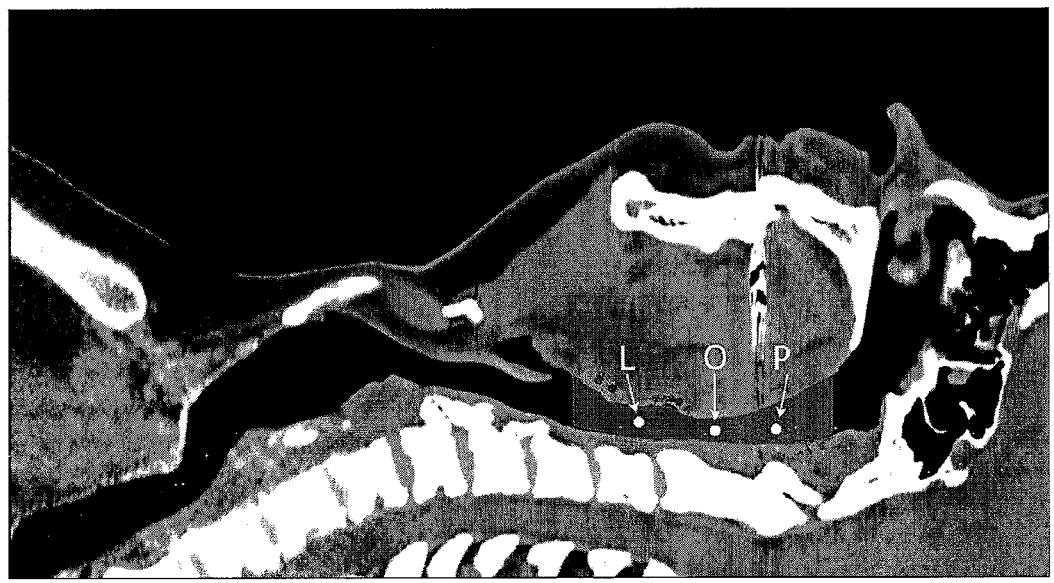
FIG. 7 Location of upper airway model.
Figure 8:
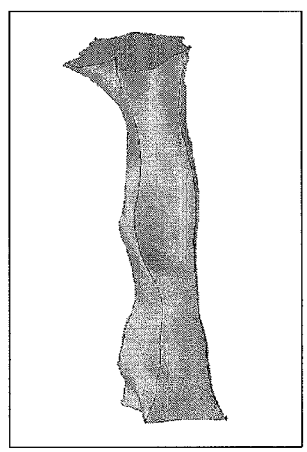
FIG. 8 Three dimensional upper airway model.

In order to make a good model it is necessary to work with a geometry that resembles the real upper airway as closely as possible. One way to achieve this is by converting a CT-scan to a CAD model, where CT images from the patient are reconstructed to form an actual three-dimensional model. The conversion has been done using Mimcs software by Materialise. FIG. 7 shows the location of the upper airway model, FIG. 8 shows the resulting 3D model.

Figure 9:
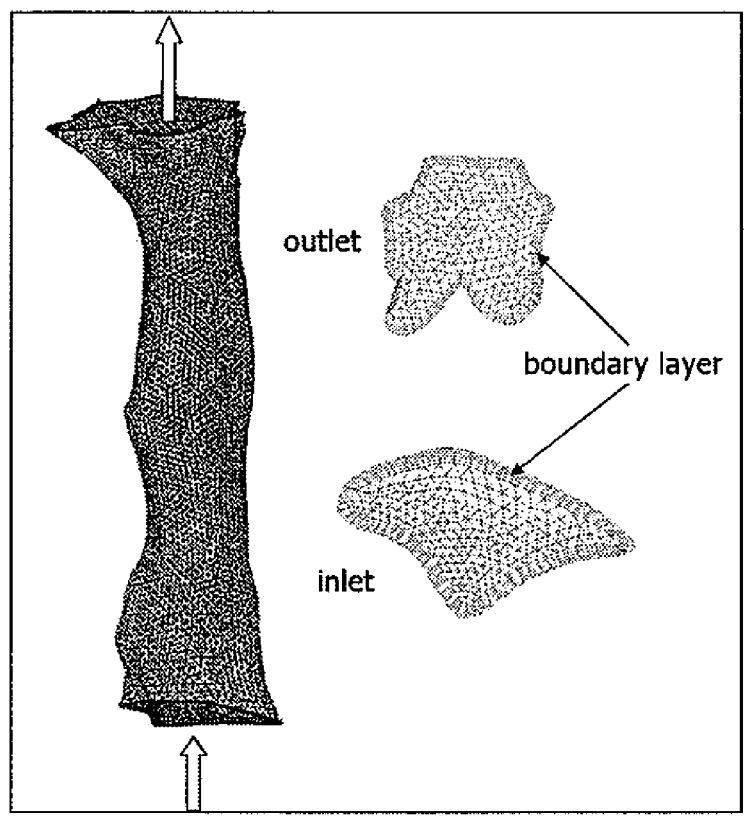
FIG. 9 Mesh for three-dimensional upper airway model.

To be able to solve the Navier Stokes equations throughout the model, the geometry has to be discretized by creating a grid. The mesh for this model, was generated with the preprocessor GAMBIT. It consists of a structured boundary layer grid and an unstructured tetrahedral grid in the middle. The boundary layer grid is included to capture the large gradients near the wall, caused by viscous effects. FIG. 9 presents the mesh, including boundary layers, for the three-dimensional upper airway model. Besides the fully meshed model a detail of the in- and outlet is given.

Example 3

Construction of 2D Model

A fully three-dimensional model requires a lot of computational power, especially when the fluid structure interaction is taken into account.

Therefore, an approximate two-dimensional model was constructed. A 2D model gives very valuable information in a much shorter period of time. Looking at the details of the in- and especially the outlet depicted in FIG. 9 the choice for a cutting plane is right through the central axis creating a near symmetry plane. FIG. 10 clarifies the choice of cutting plane.

Figure 11:
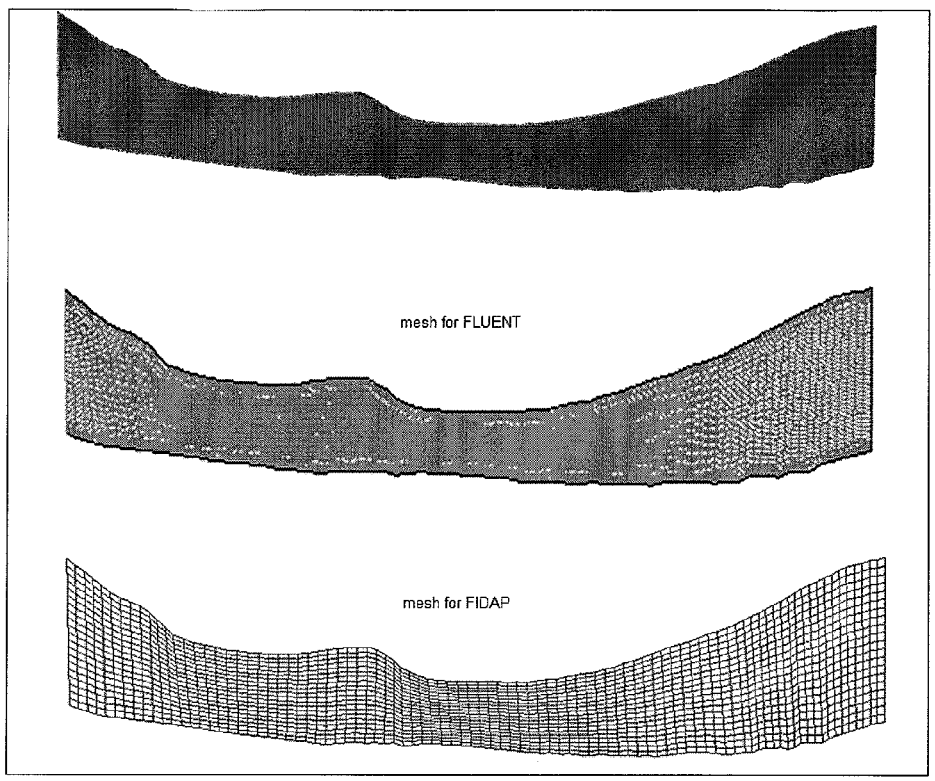
FIG. 11 Two-dimensional upper airway model.

FIG. 11 shows the two-dimensional model (upper) and the corresponding meshes for the calculations with CFD code 1 (Fluent analysis, middle) and CFD code 2 (Fidap analysis, lower). The mesh used in Fidap is less fine for several reasons. First of all the Finite Volume Method in Fluent requires a finer mesh than the Finite Element Method in Fidap. Second, the use of the zero-equation mixing length turbulence model does not impose strict requirements on a boundary layer grid. Third, the limited re-meshing capabilities in Fidap (no cells can disappear), complicate the use of a fine mesh with boundary layer. When using the finer mesh, the results diverge when the cross-sectional area decreases due to highly deformed cells. This could be solved by exporting the mesh at the moment of divergence, re-meshing the geometry and continuing the calculation. However, this is a time-consuming process and it was found that the application of a less fine mesh for the case without FSI resulted in almost exactly the same results as obtained with Fluent. Therefore, for now, the FIDAP calculations were performed with a coarser mesh.

Example 4

2D Model of Apnea Including FSI (Fidap)

The goal of this analysis is to model an expiration during which an apnea occurs using CFD code 2 analysis, implemented in this example using a "Fidap" analysis (9). In this example a 2D model takes the wall properties into account by including Fluid Structure Interactions. The properties that have to be defined are the Young's modulus E and Poisson's ratio v. The weight of the surrounding tissue is also included since this is an important aspect in the model. A combination of iterative procedures and starting values are applied to the model. An unknown value is the time function of the muscle relaxation; at the beginning of the expiration the muscles still have tension from the previous inspiration, otherwise the airway would already collapse at the point of no-flow (transition inspiration-expiration).

Boundary Conditions for 2D Model Including FSI

The boundary conditions for the flow are based on real data taken from in-patient measurements during sleep studies. The specific apnea that is modeled is discussed in Example 1.

The inlet boundary condition is a velocity inlet boundary condition. The velocity is derived from the flow measurements where the inlet area A and the density are assumed to be constant. The velocity can then be calculated using equation 1:

$$V = \frac{\dot{m}}{\rho A} \quad \text{(Eq. 1)}$$

The outlet boundary condition is set to pressure outlet. Here the pressure, also based on real data, is described. This pressure increases during expiration to overcome the nasal resistance.

Figure 12:
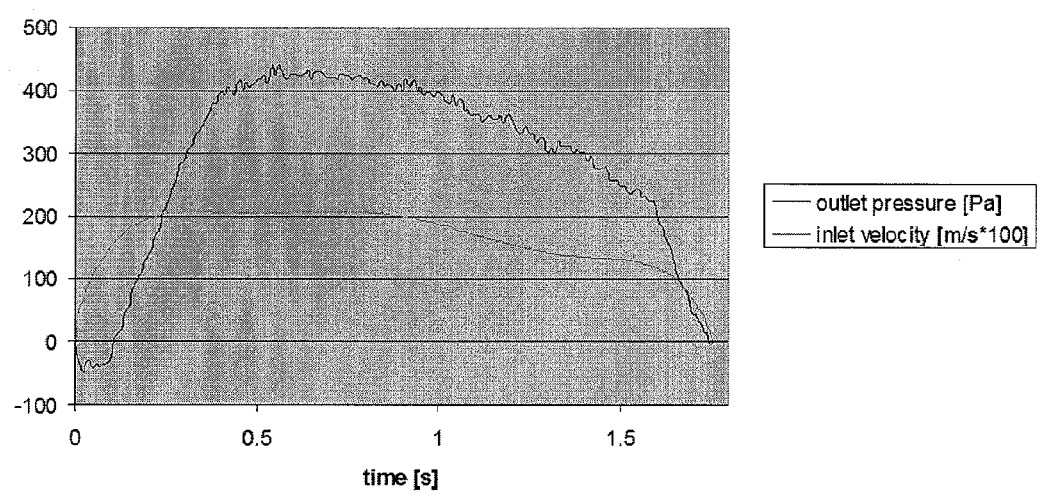
FIG. 12 Boundary conditions during expiration.

In FIG. 12, the boundary conditions during the expiration are presented. The expiration lasts 1.76s before the apnea begins. In FIG. 12 the oscillation from the Forced Oscillation Technique (FIG. 13) is removed through averaging of the flow velocity curve. There are also boundary conditions imposed on the wall. Like in the Starling resistor model (13) a part of the wall is deformable, while the other parts are fixed.

FIG. 2 presents the wall boundary conditions. The zone between B' and B" represents the deformable part of the model while the regions A'-B' and A"-B" show the non-deformable part.

This division has been chosen since at the beginning and at the end of the upper airway the surrounding structure is less deformable. That is also why it is possible to derive the velocity at the inlet when the flow is given.

The amplitude of the velocity is determined by assuming a constant inlet area. In reality there will be a slight variation in inlet area, but this variation is limited in comparison with the variation at the points L, O and P.

The velocity defined at the inlet is uniform. This means that no boundary layer profile is applied (no fully developed flow), while this will be present in reality. Furthermore, specific flow characteristics, caused by the irregularities discussed above, are ignored.

The pressure defined at the outlet is an approximation, since the accuracy of the pressure measurements is limited as explained in Example 1. The choice of the deformable region might influence the shape of the deformation.

Wall Properties for 2D Model Including FSI

The value for the Young's modulus varied between 20000 and 100000 for the wall. In this model the young's modulus is assumed to be linear. Wuyts (14) and Ishono (15, 16) show that human tissue has a non-linear behaviour when stretched, especially in the region where the collagen component is dominant. However during a collapse of this tissue the elastin/smooth muscle component is dominant, resulting in a more linear behaviour. The Poisson's ratio is not an important factor in a 2-dimensional model. It represents the ratio between lateral and axial strain (17). In a 2D model the lateral strain is not present. The model shows a collapse at the end of the expiration when a weight of approximately 1.85 kg is applied to the upper airway. Increasing the weight to 2.4 kg shows a full closure of the airway. Decreasing the weight, however, results in an airway that is still open at the end of the expiration. The weight itself is an unknown and is determined through an iterative process.

It is clear that a few additional approximations are introduced:

The Young's modulus is taken to be a constant during expiration, while in reality the tissue will behave non-linearly.
The weight of the surrounding tissue is not known exactly.
The time function for the muscle relaxation cannot be fully determined in advance.

Results for 2D Model Including FSI

Figure 13:
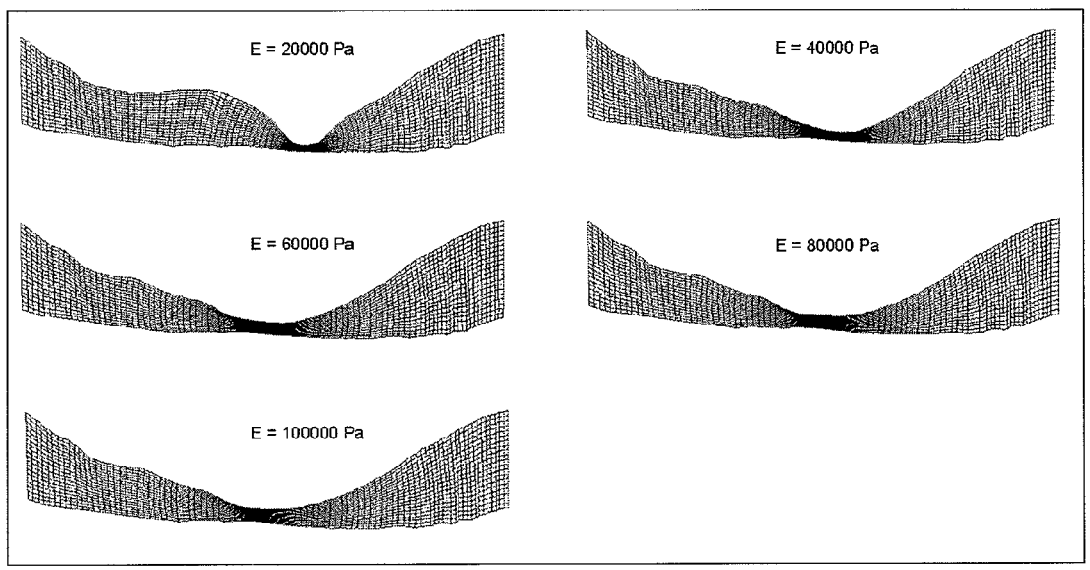
FIG. 13 Deformation of upper airway for different Young's moduli, weight=1.85 kg.

FIG. 13 shows how the upper airway deforms for different Young's moduli with a weight of 1.85 kg. It is clear that increasing the Young's modulus (E) results in a more evenly distributed deformation, For E=20000 the effect of the intraluminal pressure $P_{in}$ is much larger, resulting in a more narrow region of collapse.

When $P_{in}$ is larger than the surrounding tissue pressure the airway is forced to open. In reality the expansion is constraint by the surrounding tissue. This natural constraint, is not present in this model, however, it is within the scope of the invention that the current model can be refined by modelling the surrounding structure more accurately and thereby adding this constraint. This can be necessary when trying to model the effect of nCPAP. The nCPAP pressure is determined to keep that the upper airway open under all conditions. When applying this additional pressure to the model as it is now, the airway would expand due to a lack of tissue resistance.

Figure 14:
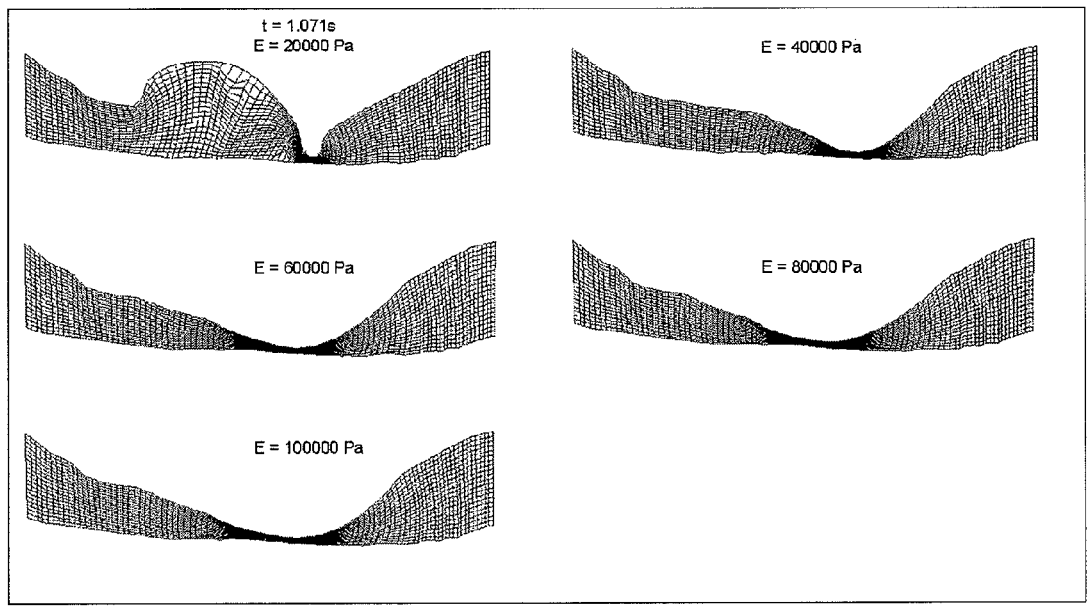
FIG. 14 Deformation of upper airway for different Young's moduli, weight=2.44 kg.

This phenomenon can be seen in FIG. 14 where for a weight of 2.44 kg and a Young's modulus of 20000 the intraluminal pressure $P_{in}$ becomes so high that the airway expands. The mesh becomes thoroughly distorted and the simulation stops due to a lack of convergence at t=1.071s.

When comparing FIGS. 13 and 14 the modeling shows that increasing the weight increases the amount of collapse. This is in agreement with what one expects.

Figure 15:
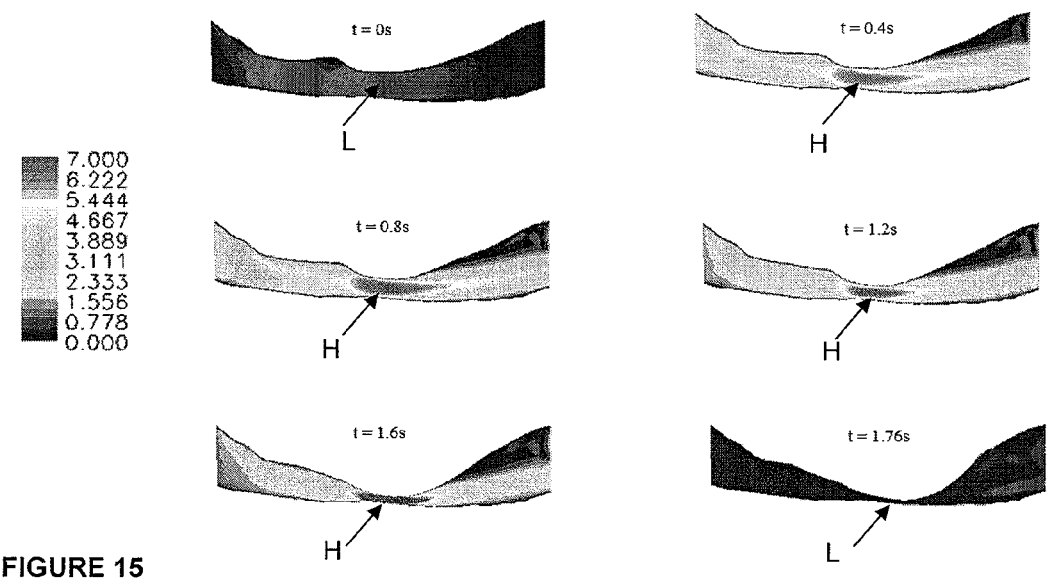
FIG. 15 Velocity contours [m/s] in 2D model with FSI, weight=2.44 kg, E=100 000.
Figure 16:
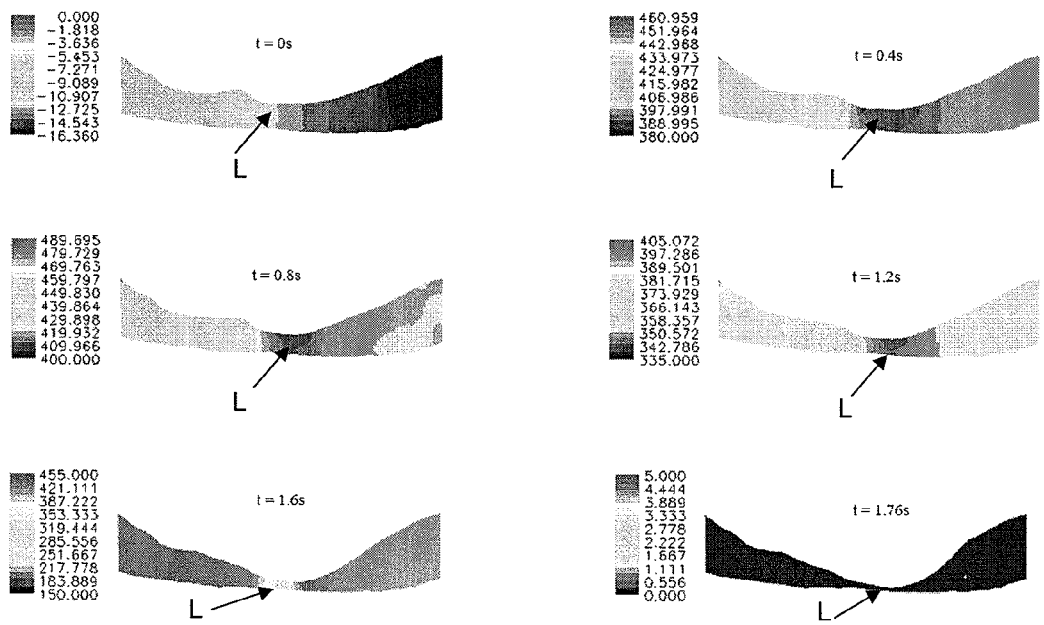
FIG. 16 Pressure contours [Pa] in 2D model with FSI, weight=2.44 kg, E=100 000.

In FIG. 15 and FIG. 16 the velocity and pressure contours respectively are given at different time steps.

It is clear that in the narrowest part of the airway the velocity is highest (FIG. 15, H) due to the Venturi effect; it is low (FIG. 15, L) at the start and after collapse. Consequently, according to Bernoulli's law, the pressure will be lowest in that region (FIG. 16, L). The high velocity and low pressure region is sustained by the partial collapse. Although the velocity at the inlet decreases, the velocity in the narrowest section will remain high due to decreasing area. Once the cross-sectional area decreases, pressure will built up in the upstream part of the airway (FIG. 16, t=1.6 s), due to the higher resistance. This also explains the expansion shown in FIG. 15 for E=20000 Pa.

Figure 17:
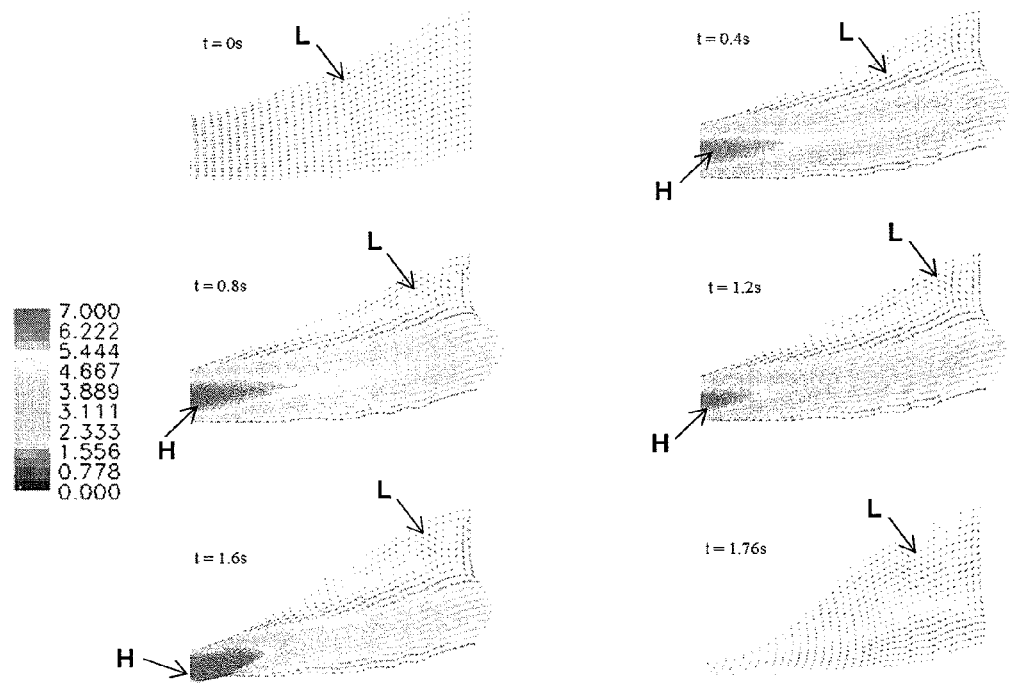
FIG. 17 Velocity vectors [m/s] in 2D model, with FSI.

FIG. 17 presents the velocity vectors for the model where in regions of high (H) and low (L) velocity are indicated. A region of separation and recirculation can be seen just after the narrowest section.

Example 5

Validation of Results 2D Model Including FSI

Figure 18:
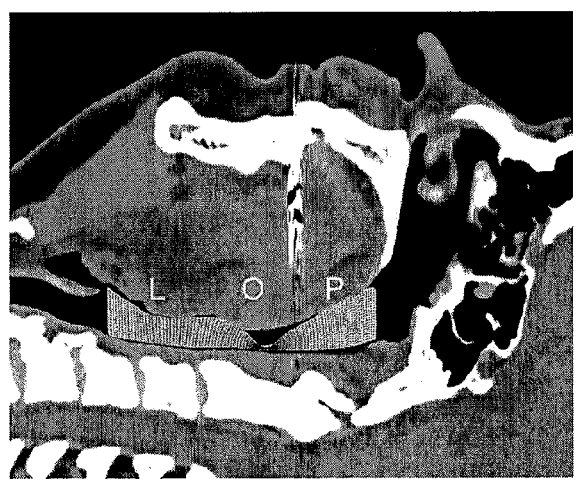
FIG. 18 Location of upper airway collapse in computer flow dynamic model (CFD).

It is quite difficult to validate the results of the CFD model. The accuracy of the pressure measurements with the catheter is not high enough to rely on the absolute values. However since the pressure is measured at different locations, the measurements can give a good indication of the position of collapse: collapse occurs between the point where a pressure signal is still measured during apnea and the next point downstream. The patient's data showed that the location of collapse is very often between the palato- and the oropharynx (position P and O in FIG. 18) and it is also at this location that the CFD model predicts the collapse.

Figure 19:
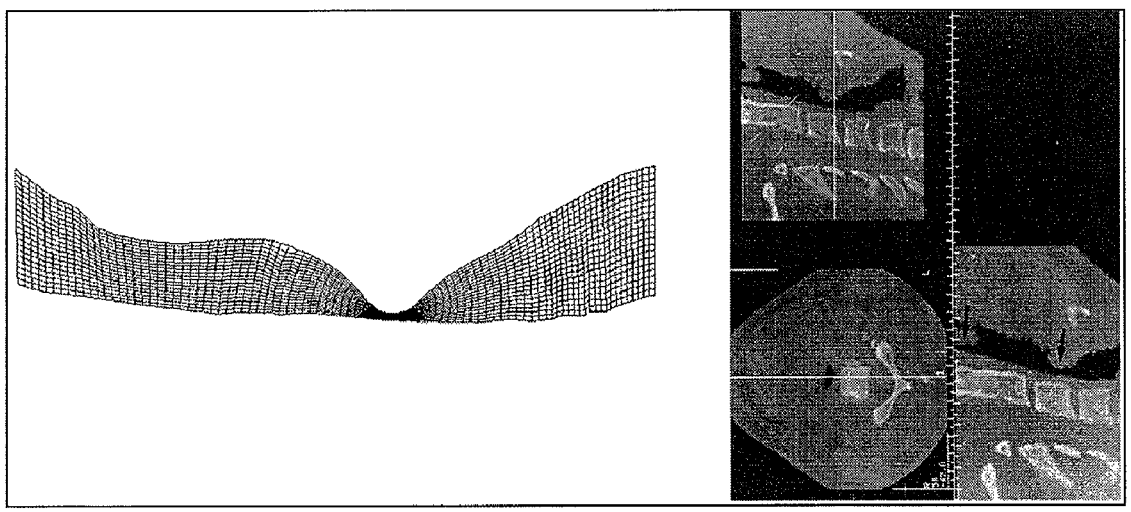
FIG. 19 Validation of computer flow dynamic upper airway model with computer tomography images.

Visualisation of an upper airway narrowing or collapse using CT or MRI techniques is complex, although not impossible. Caballero (18) succeeded in doing so as depicted in FIG. 19 on the right. Comparing this to the collapse of the CFD model (tissue weight 2.4 kg, E=20000 Pa) one can see that the way the model collapses is similar to the collapse in the CT images. This can be an indication that the young's modulus of the tissue will be in the lower range. The patient that was used to make the CFD model is different from the person in the CT scan in FIG. 19.

The use of the Forced Oscillation Technique (5) (FOT) can also be a way to validate the model. This technique continuously measures the impedance Z of the upper airway during the sleep study. Changes in the impedance Z reflect changes in the airway patency. A positive slope of the Z/Z_osa curves represents a closure of the upper airway; a negative slope indicates an opening of the upper airway.

Vanderveken (19) (FIG. 20 top) has shown that it is mainly during the final part of the expiration that the impedance increases and thus the upper airway collapses.

Figure 20:
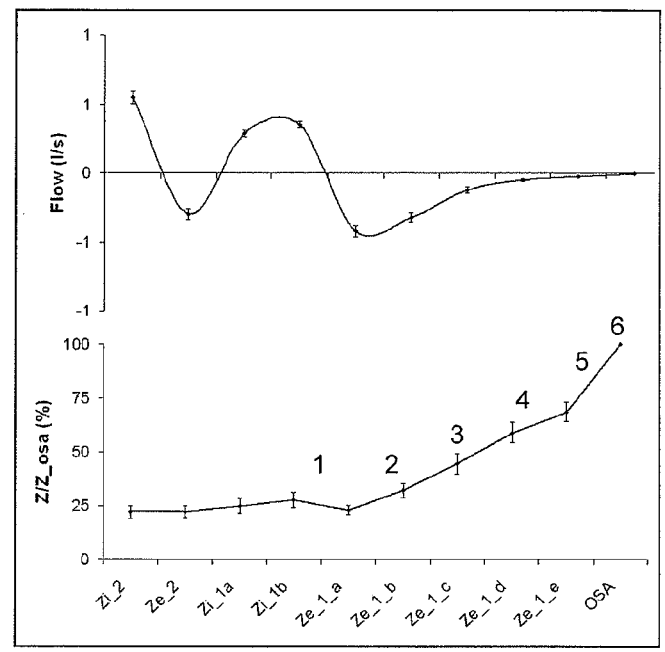
FIG. 20 Validation of CFD upper airway model (lower) with forced oscillation technique (FOD) impedance measurements (upper).
Figure 20:
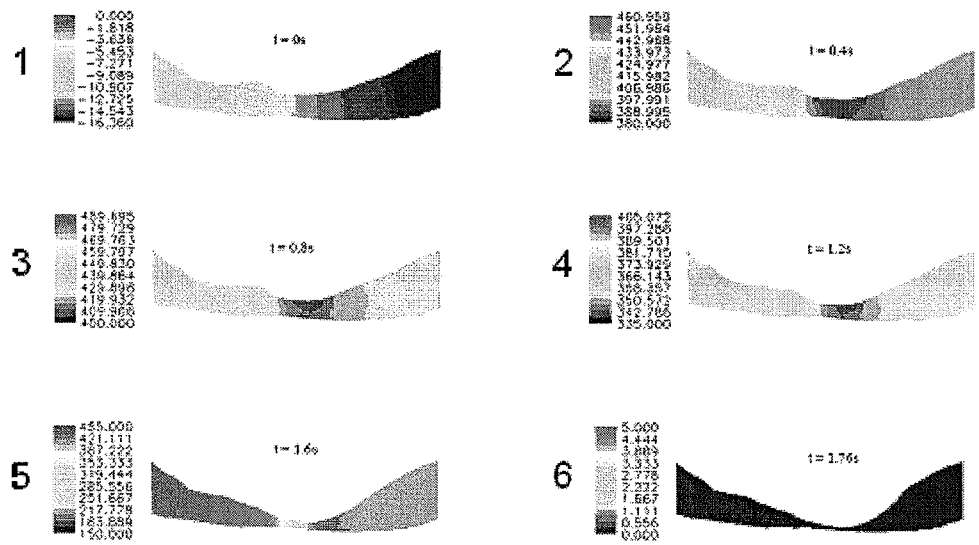

In FIG. 20 a comparison is made between the collapse of the CFD model (weight=2.4 kg, E=100 000 Pa) and a real measurement using the above mentioned FOT technique. One can see that in both cases the collapse occurs at the end of the expiration. The explanation lies in the fact that at that moment the weight on the airway is maximal due to the muscle relaxation and the intraluminal pressure goes to zero (FIG. 12). The slope of this pressure curve is quite steep at the end, explaining why the impedance rises faster between point 5 and 6. The patient that was used for the CFD model also was part of the study using the forced oscillation technique.

Example 6

Analysis of Flow Properties and Boundary Conditions (Fluent)

The goal of the modelling with CFD code 1 (implemented using Fluent (8) in these examples) is to obtain an initial estimate of the flow properties during a normal expiration (when the variation in geometry is limited) and to investigate the applicability of the 2D model. The flow through the model is unsteady, viscous and incompressible. The Reynolds number, based on the mean diameter of the tube at the time of maximum flow is in the order of 6000. As indicated in literature (6, 7) the flow in the upper airway is turbulent at this Reynolds number. The turbulence model used for this initial analysis is the one-equation Spalart-Allmaras model (8). The application of this model will not increase the computational time too much and it allows a reasonable comparison with the FIDAP calculations where the zero-equation mixing length model (9) is used. It can be expected that a two-equation model such as the realizable k-ε model (8) will result in more accurate results, but the computational time, mainly for the 3D model and the FIDAP calculations, will increase considerably.

The boundary conditions are set to velocity inlet and pressure outlet, to account for the nasal resistance. The expiration shown in FIG. 5 is approximated by assuming a sine function for both conditions. The duration is 3 seconds, the amplitude of the pressure variation is 200 P and the amplitude of the velocity variation is determined by using the measured flow rate and the following relation: ṁ=ρAV. In this formula ṁ is the mass flow rate, ρ is the density of the air and V is the velocity.

This results in the following formulas for the boundary conditions:

$$V_{in}(t) = 1.8375\sin\left(\frac{\pi}{3}t\right) \quad \text{(Eq. 2)}$$

$$P_{out}(t) = 200\sin\left(\frac{\pi}{3}t\right) \quad \text{(Eq. 3)}$$

The application of these boundary conditions introduces some inaccuracies:
  The sine function does not exactly correspond to the profile shown in FIG. 5 but the approximation is sufficient for the purpose of this analysis.
  The amplitude of the velocity is determined by assuming a constant inlet area. This assumption is made in every analysis in this report. In reality there will be a slight variation in inlet area, but this variation is limited in comparison with the variation at the points L, O and P.
  The velocity defined at the inlet is uniform. This means that no boundary layer profile is applied (no fully developed flow), while this will be present in reality. Furthermore, specific flow characteristics, caused by the irregularities in the preceding sections, are ignored. When observing the specific shape right before and at the inlet it can be seen that separation is not likely to occur at the inlet, but the inaccuracy has to be kept in mind when interpreting the results. It might be useful to do a more extensive flow analysis starting from the end of the trachea, where flow separation does not occur.
  The amplitude of the pressure outlet is an approximation, since the accuracy of the pressure measurements is limited as explained above. For the present analysis this approximation is expected to be sufficient.

Example 7

Fluent Analysis—3D Model of Normal Expiration

Figure 21:
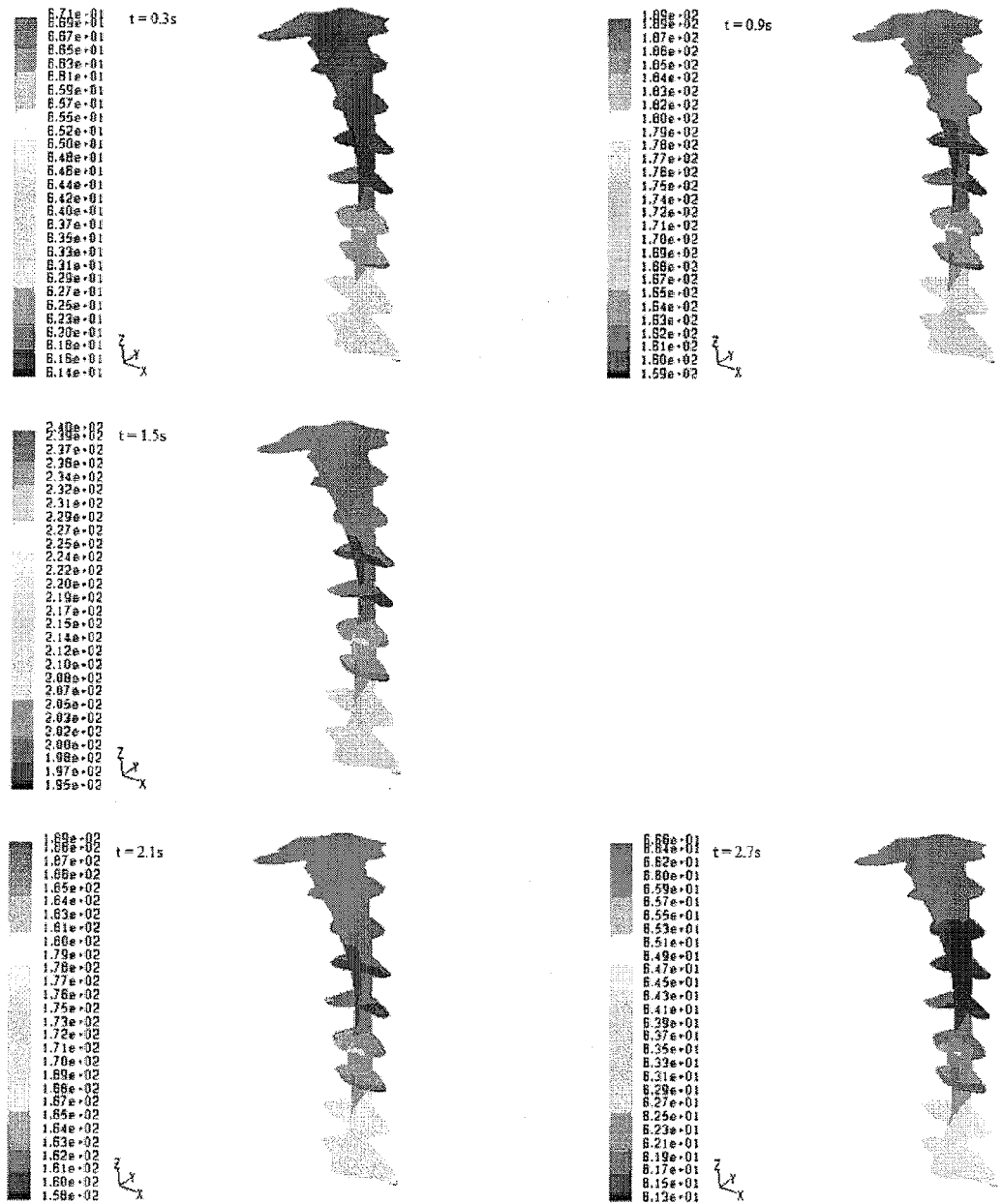
FIG. 21 Pressure contours [Pa] in upper airway.
Figure 22:
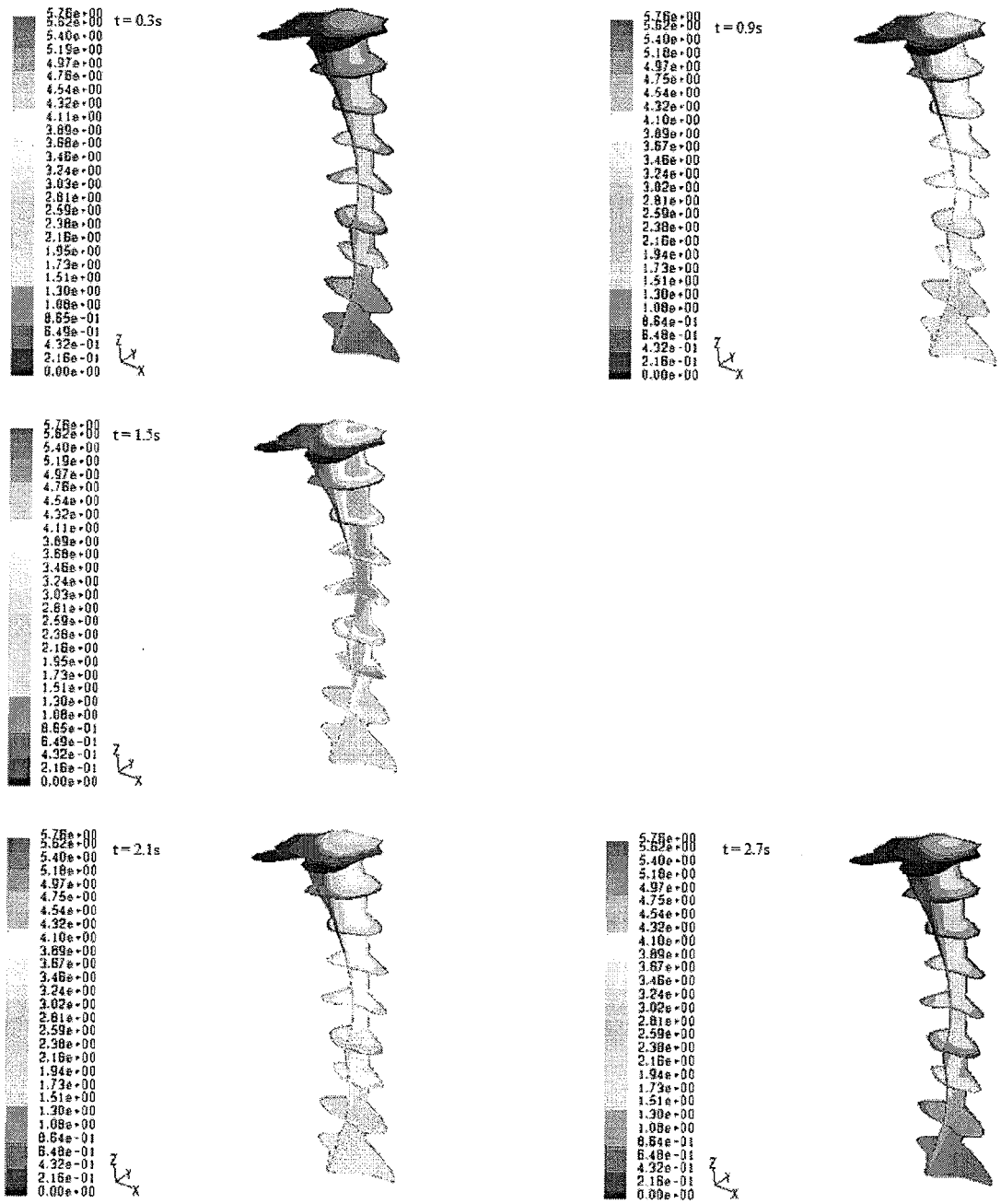
FIG. 22 Velocity contours [m/s] in upper airway.
Figure 23:
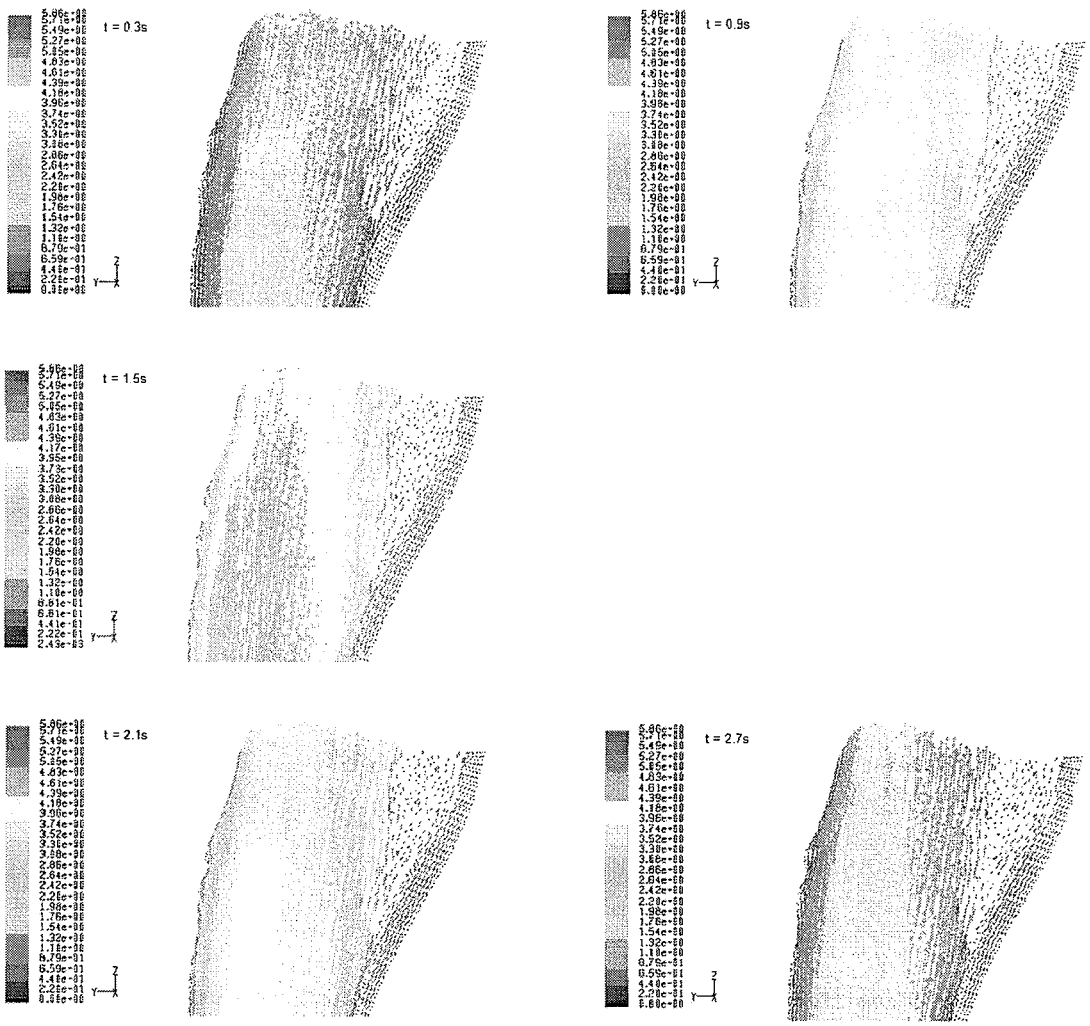
FIG. 23 Close-up of velocity vectors [m/s] in y-z plave in upper airway.

The results for the 3D model are shown in FIGS. 21, 22 and 23. The results were checked for grid- and time step dependency. A refinement of the grid did not change the results; neither did a reduction of the time step from 0.01 s to 0.005 s.

FIG. 21 shows contours plots of the pressure at different time levels. From this figure it is obvious that the main pressure difference occurs over time due to the variation in outlet pressure (to overcome the nasal resistance). When neglecting the build up of pressure at the inlet, which is not present in reality, the variation relative to the outlet pressure is limited to ±10 Pa. This is also an indication that the decrease in pressure due to the narrowing of the geometry can not be solely responsible for the occurrence of an apnea, since a CPAP pressure of 588 Pa is required to prevent collapse. Once a collapse is initiated and a further narrowing occurs, the pressure decrease will become more significant.

FIG. 22 shows the velocity increase in the narrowest section, which is inherent to the pressure decrease. The figure also shows the appearance of a recirculation region in the upper section.

In order to improve the visualization of the separation region, FIG. 23 shows the velocity vectors near the outlet in the y-z plane at different time steps.

From this initial analysis one can conclude that, besides the pressure decrease in the narrow sections, an additional force is required to initiate a collapse. This force originates from the relaxation of the muscles during expiration, which results in an increasing pressure exerted on the airway wall by the surrounding tissue (e.g. the tongue (10, 11, 12). In FIG. 7 it is shown that the largest amount of tissue mass is located above the airway. This explains why most apneas occur when the patient is lying on his back. The reduction to the 2D model, as discussed in Example 3, therefore represents the 'worst case scenario'.

Example 8

Fluent Analysis—2D Model of Normal Expiration

Figure 24:
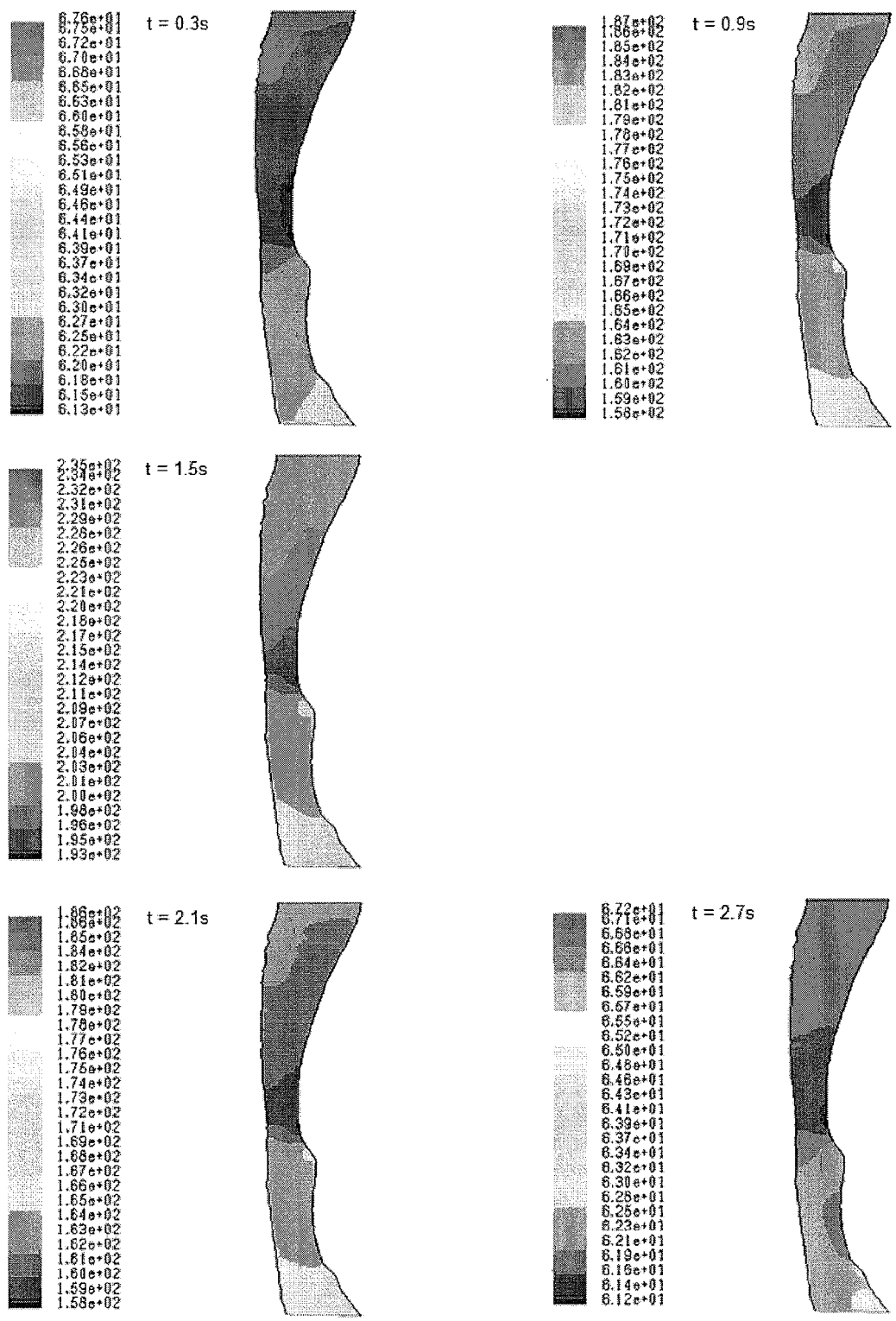
FIG. 24 Pressure contours [Pa] in 2D model.
Figure 25:
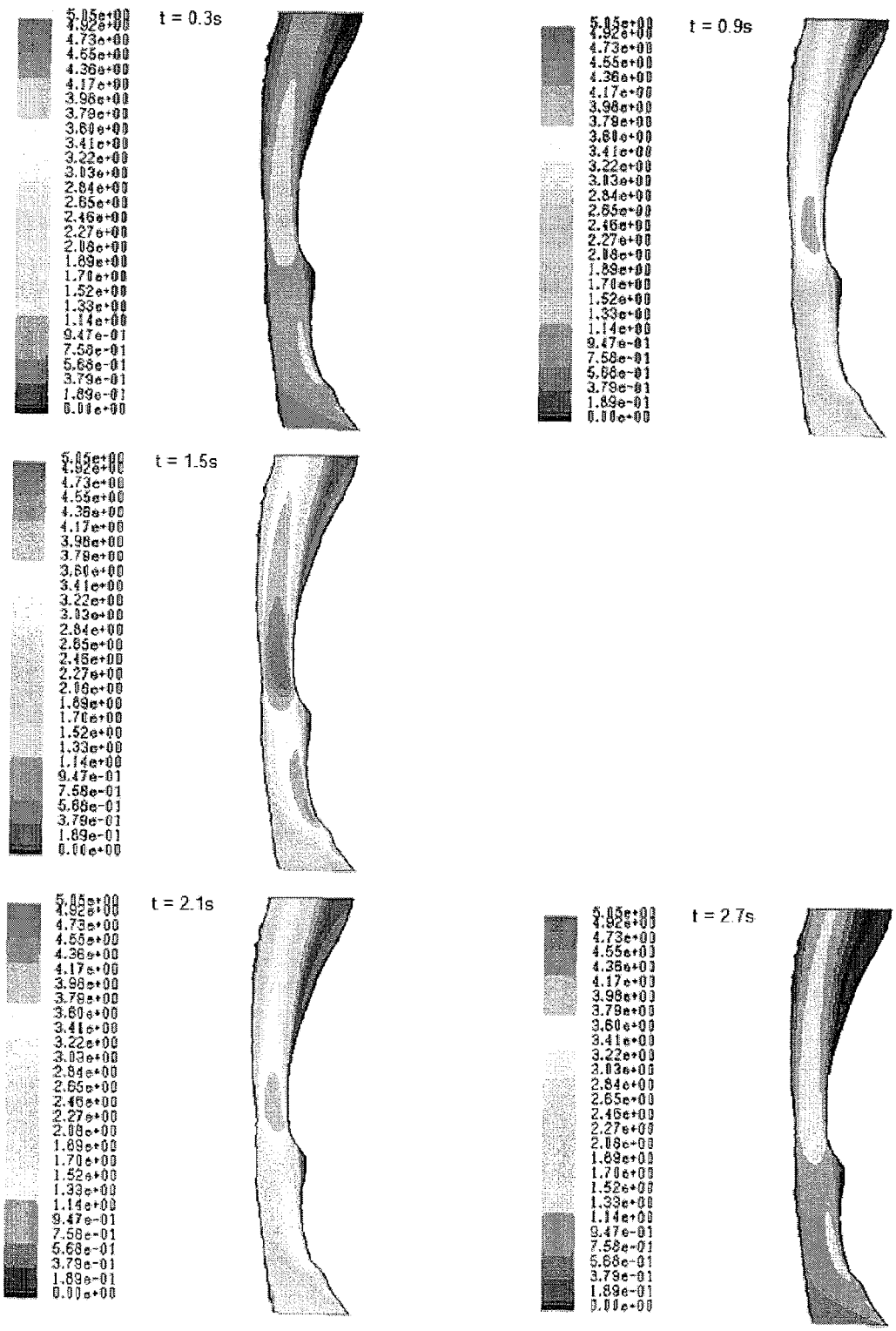
FIG. 25 Velocity contours [m/s] in 2D model.
Figure 26:
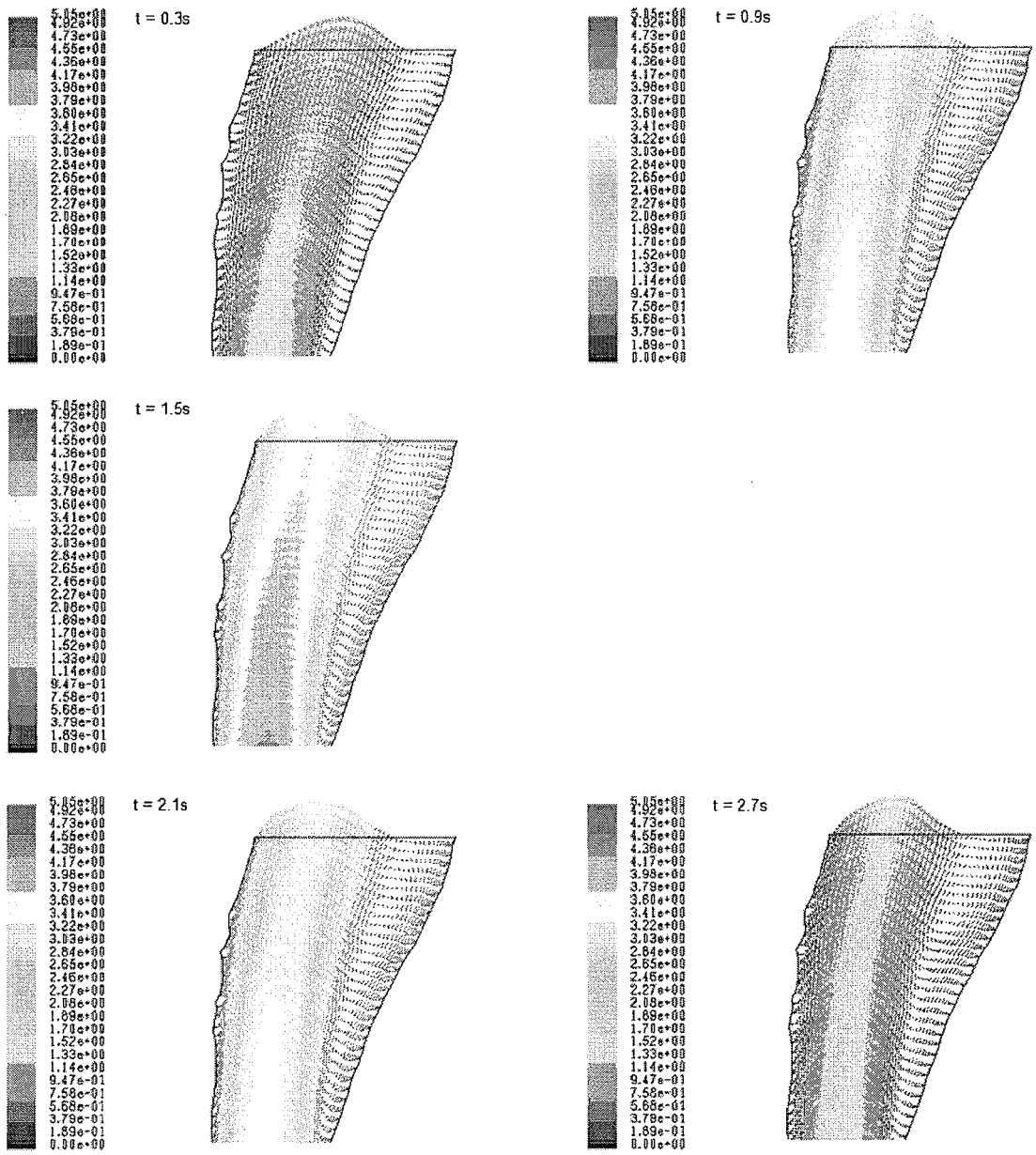
FIG. 26 Velocity vectors [m/s] in 2D model.

The results of the 2D model are shown in FIGS. 24, 25 and 26. FIG. 24 shows the pressure contours and when comparing those with FIG. 21, it can be concluded that the range is comparable. In the 3D model the maximum pressure is higher due to the larger build up of pressure in the lower right corner. The lowest pressure, which is more important when predicting collapse, is almost exactly the same.

FIG. 24 shows the velocity contours. The maximum velocity is slightly higher in the 3D model, but this velocity does not occur in the y-z plane. The maximum value in the y-z plane is close to the maximum value predicted by the 2D model. The 2D model also shows separation in the same region as the 3D model. The velocity vectors are displayed in detail in FIG. 25.

Figure 27:
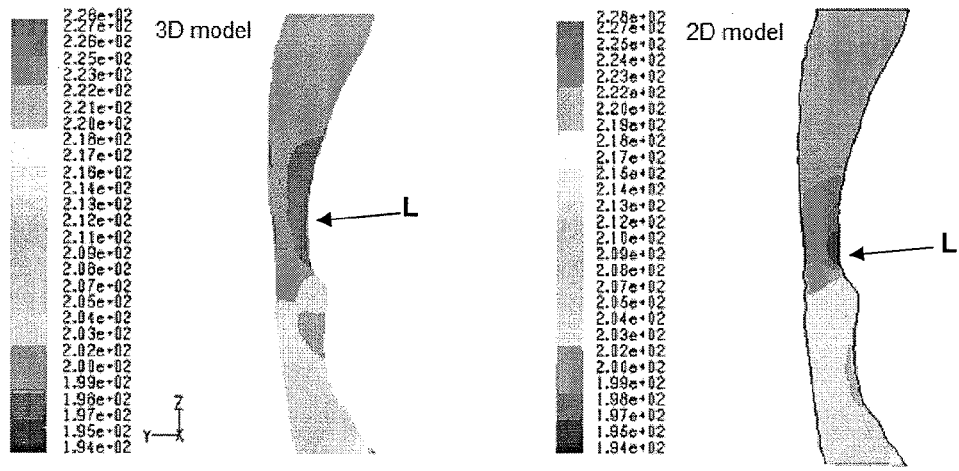
FIG. 27 Comparison of pressure contours [pa] for 3D and 2D model at t=1.5 s.
Figure 28:
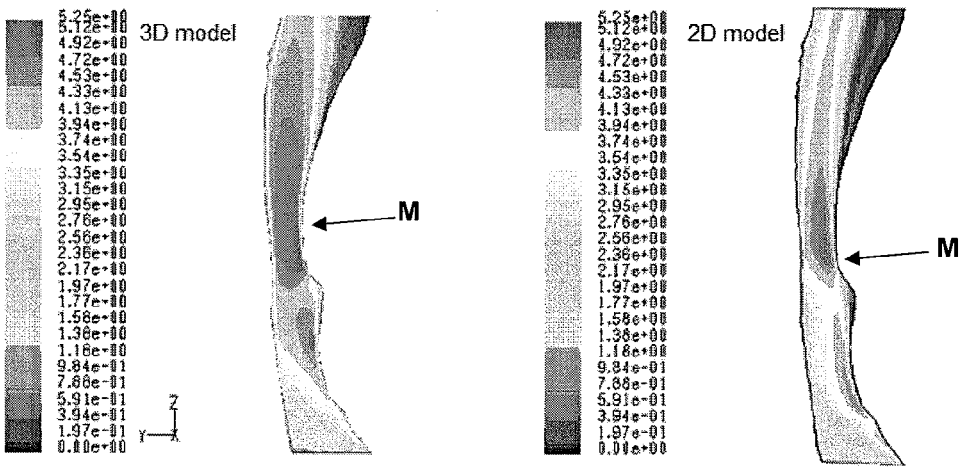
FIG. 28 Comparison of velocity contours [m/s] for 3D and 2D model at t=1.5 s.

In order to compare the profiles of the contours, FIGS. 27 and 28 show a comparison of the pressure and velocity contours at the time of maximum flow.

FIG. 27 shows that the pressure decreases slightly faster in the 2D model. In this model the minimum pressure is slightly lower and more concentrated in the narrowest section (L). In the 3D model the minimum pressure (L) occurs in a slightly larger region. This is easily explained by the fact that, although the cross-section in the y-z plane increases, the cross-sectional area in 3D remains small.

FIG. 28 shows that the maximum velocity in the 3D model (M) is slightly higher and occurs in a larger region. This is again explained by the difference in cross-sectional variation when looking at the y-z plane instead of the 3D model. The separation region in the y-z plane is slightly larger in the 2D model. Despite these differences the overall profile compares reasonably well.

From these results, it is expected that the reduction to 2D will give a good approximation when modeling the Fluid Structure Interactions.

From examples 6, 7 and 8, two major conclusions can be drawn:
1. The pressure variation over the airway caused by a narrowing of the cross-sectional area is limited. The variation is an order of magnitude smaller than the CPAP pressure required to prevent airway collapse. It can therefore be concluded that pressure variations induced solely by the flow can not initiate a collapse. An additional reason for collapse can be found in the relaxation of the muscles during expiration and consequently the increasing pressure exerted on the airway wall by surrounding tissue (e.g. the tongue (10, 11, 12)). It will be necessary to incorporate this tissue mass and the relaxation of the muscles over time to simulate a collapse.
2. The reduction to 2D will result in a large reduction in computational time and is still expected to give a good approximation. First of all, the velocities perpendicular to this plane are almost zero, since the y-z plane is a near symmetry plane. Second, this case represents the 'worst case scenario', since most apneas occur when the patient lies on his back. Third, a comparison of the 3D and 2D results shows a reasonable agreement in both the range and the profile of the pressures and velocities. Therefore, the analyses with Fidap will be performed for the 2D model. However, it must be kept in mind that it could be possible that the lateral airway walls collapse. Since this is not included in the 2D model, a 3D analysis might be performed in a later stage to further verify the 2D results.

Example 9

2D Model of Normal Expiration without FSI

The goal of this analysis is to compare the results for a normal expiration obtained with FIDAP with the results shown previously.

The boundary conditions are equivalent to the ones described in equations 2 and 3. This implies that the inaccuracies mentioned in Example 6 are also present in this analysis.

Figure 29:
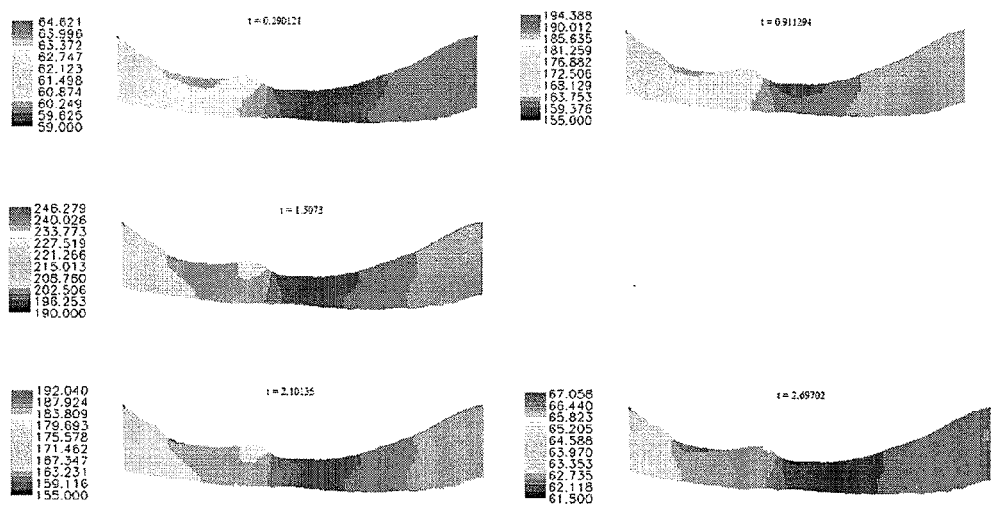
FIG. 29 Pressure contours [Pa] in 2D model, no FSI.

FIG. 29 shows the pressure contours. Both the range and the profile are comparable to the solution obtained with Fluent.

Figure 30:
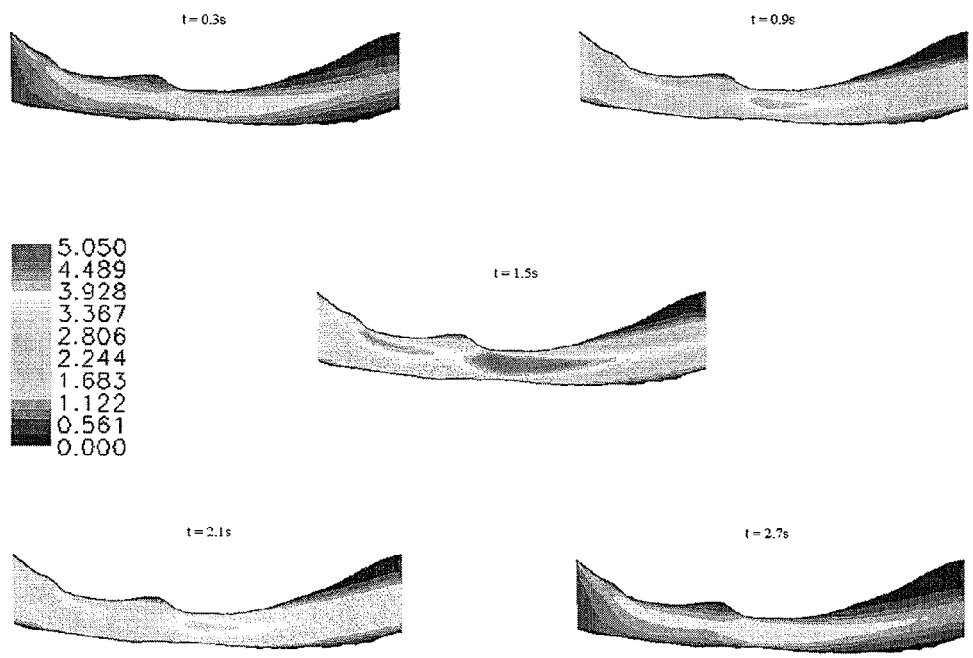
FIG. 30 Velocity contours [m/s] in 2D model, no FSI.

FIG. 30 shows the velocity contours and, as expected, these also correspond to the contours shown in FIG. 25.

Figure 31:
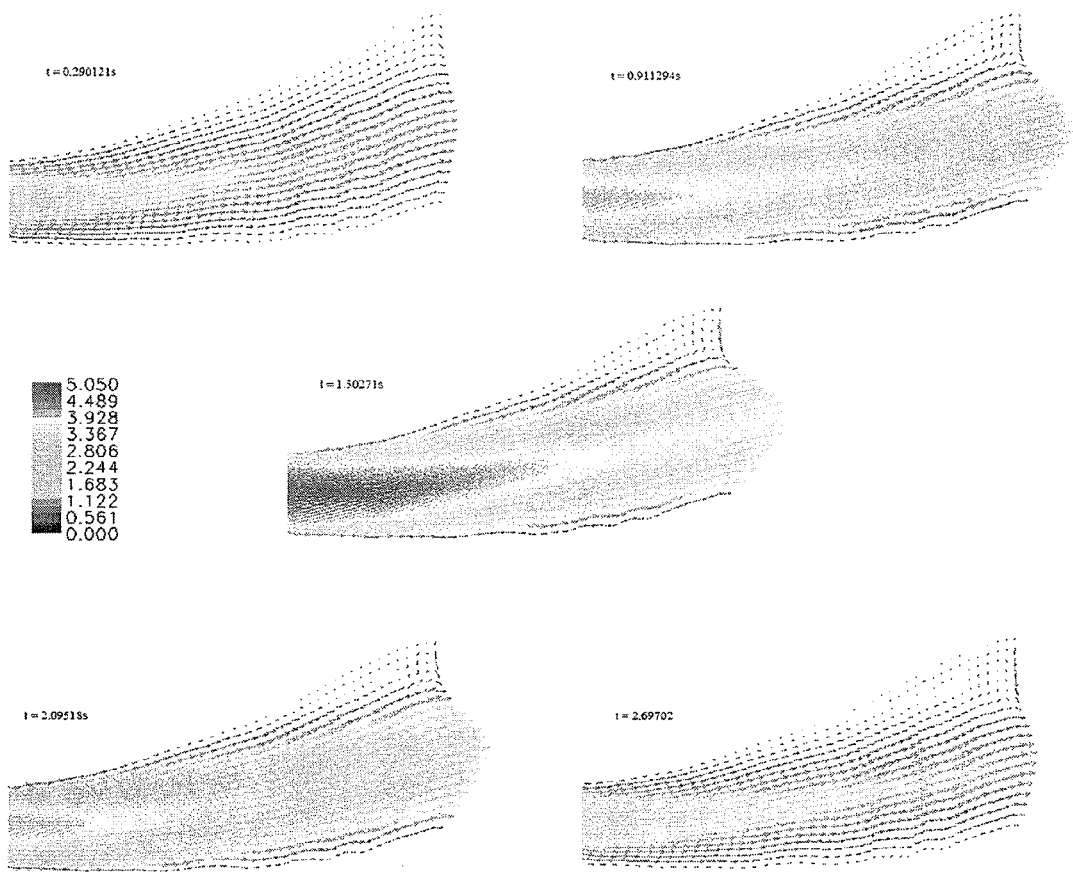
FIG. 31 Velocity vectors [m/s] in 2F model, no FSI.

The velocity vectors are displayed in FIG. 31 to clarify the separation region.

The conclusion of this analysis is that the solution for the flow only is the same in FIDAP as in FLUENT. Since this already validates the results, no time or grid independency study was performed.

The validation of the 2D model was threefold:
The location of the collapse was validated using the pressure measurements obtained during sleep studies. These measurements frequently showed a collapse around the oropharynx. The upper airway closure in the CFD model also occurred at that location.

The shape of the collapse was validated by comparison of the CFD model with CT scans taken from patients with upper airway narrowing. The shape of the collapse in the CFD model resembled the CT scans quite well.

The validation was done using the Forced Oscillation technique. With this technique the impedance of the upper airway can be measured. Impedance is a measure for the closure of the upper airway. Using this technique the timing of the collapse can be validated. When comparing the model and the FOT it became clear that the collapse occurs during the second phase of the expiration when the relaxation of the muscles is maximal and the pressure due to the nasal resistance decreases to zero. Both the CFD model and the FOT illustrated this trend and were in accordance.

Looking at these validations one can conclude that the model is behaving correctly.

Example 10

Further Validation of Computational Fluid Dynamics Analyses

Another validation of the CFD analyses of the present invention is made by comparing simulated data with in-patient measurements. A total of 4 patients was examined:
Patient VDB
Patient JT
Patient AL
Patient VVM For each of the cases the flow inside the upper airway between the palato- and hypopharynx was modelled with and without a mandibular advancement device (MAD). The pressures throughout the models were analysed and compared for both scenarios. For the comparison the pressures were taken at the same location for consistency. Subsequently polysomnography (PSG) data was examined and the number of apneas (apnea index, AI) was determined before and after the implementation of the MAD device.

Figure 32:
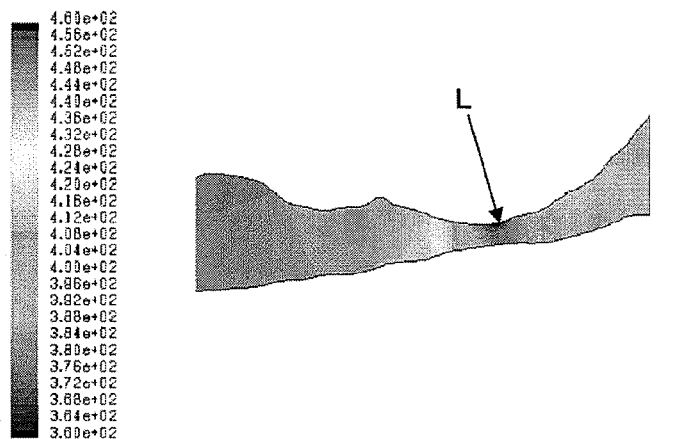
FIG. 32 Pressure contours and apnea index of patient VDB, before and after fitting with MAD.
Figure 32:
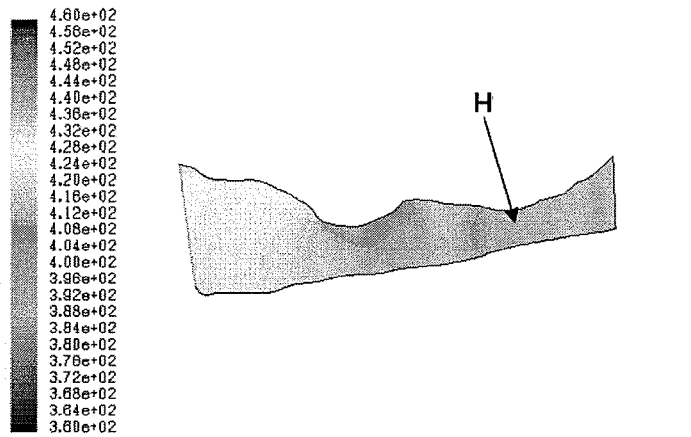
Figure 32:
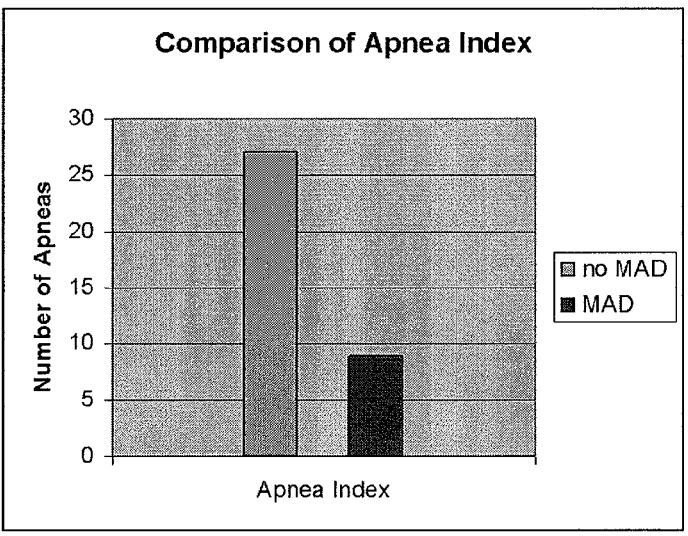

The results are shown in FIGS. 32 to 35. FIG. 32 shows the CFD models generated by the present invention in patient VDB without a MAD (A) and with a MAD (B). Patient VDB is a 48 year old male, with a body mass index (BMI) of 27. Indicated at position (L) is the narrowest cross-sectional area which is predicted to experience an increase in pressure (H) when the MAD is fitted. For reference, the pressure at point L is in the region of $3.64 \times 10^2$ Pa, rising to around $3.88 \times 10^2$ Pa (H) in the presence of a MAD. The pressure difference is +30 Pa at expiration peak flow. FIG. 32(C) shows a decrease in the AI after fitting (measured by PSG), attributable to a pressure increase at the narrowest cross-sectional area.

Figure 33:
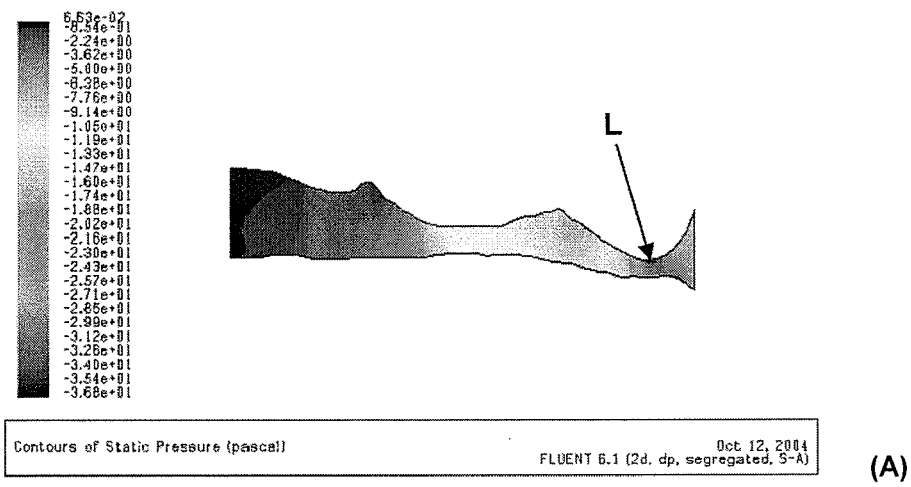
FIG. 33 Pressure contours and apnea index of patient JT, before and after fitting with MAD.
Figure 33:
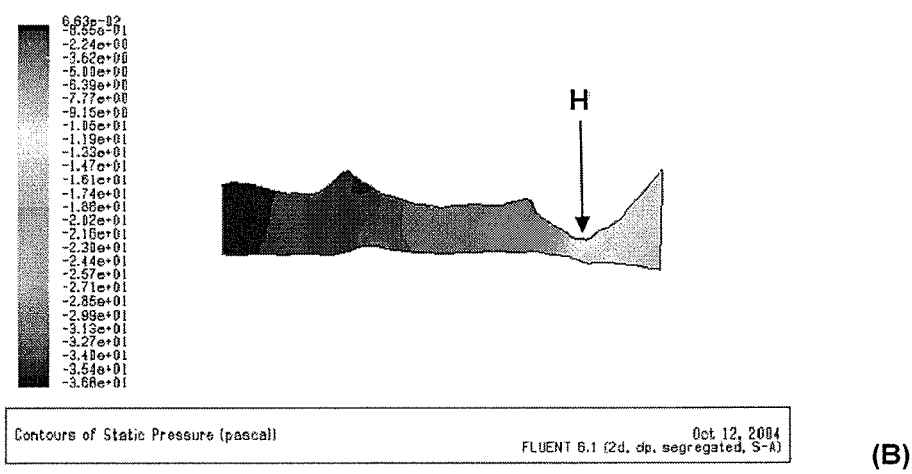
Figure 33:
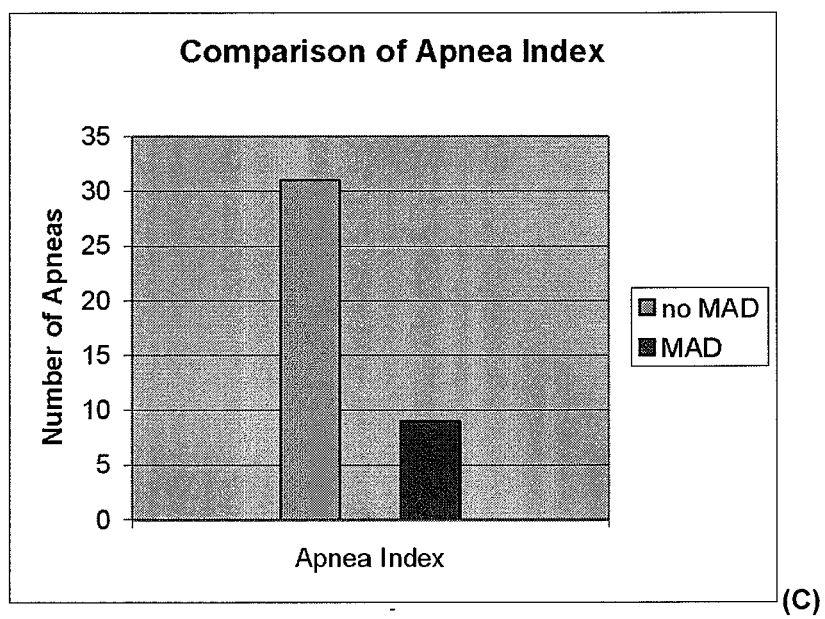

FIG. 33 shows the CFD models generated by the present invention in patient JT without a MAD (A) and with a MAD (B). Patient JT is a 60 year old male, with a BMI of 34. Indicated at position (L) is the narrowest cross-sectional area which is predicted to experience an increase in pressure (H) when the MAD is fitted. For reference, the pressure at point L is in the region of $-3.54 \times 10^1$ Pa, rising to around $-1.19 \times 10^1$ Pa (H) in the presence of a MAD. The pressure difference is +26 Pa at expiration peak flow. FIG. 33(C) shows a decrease in the AI after fitting (measured by PSG), attributable to a pressure increase at the narrowest cross-sectional area.

Figure 34:
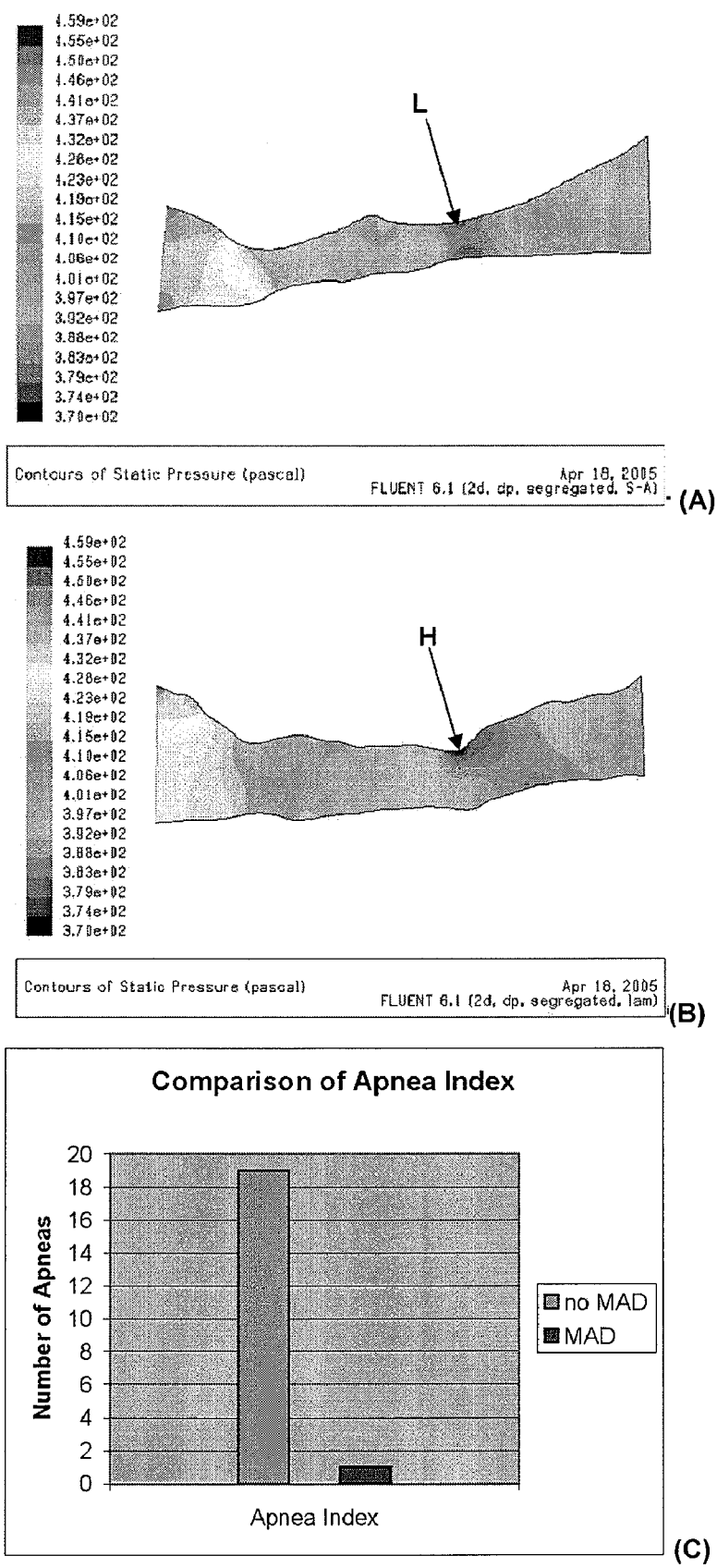
FIG. 34 Pressure contours and apnea index of patient AL, before and after fitting with MAD.

FIG. 34 shows the CFD models generated by the present invention in patient AL without a MAD (A) and with a MAD (B). Patient AL is a 44 year old male, with a BMI of 25. Indicated at position (L) is the narrowest cross-sectional area which is predicted to experience an increase in pressure (H) when the MAD is fitted. For reference, the pressure at point L is in the region of $3.88 \times 10^2$ Pa, rising to around $4.01 \times 10^2$ Pa (H) in the presence of a MAD. The pressure difference is +18 Pa at expiration peak flow. FIG. 34(C) shows a decrease in the AI after fitting (measured by PSG), attributable to a pressure increase at the narrowest cross-sectional area.

Figure 35:
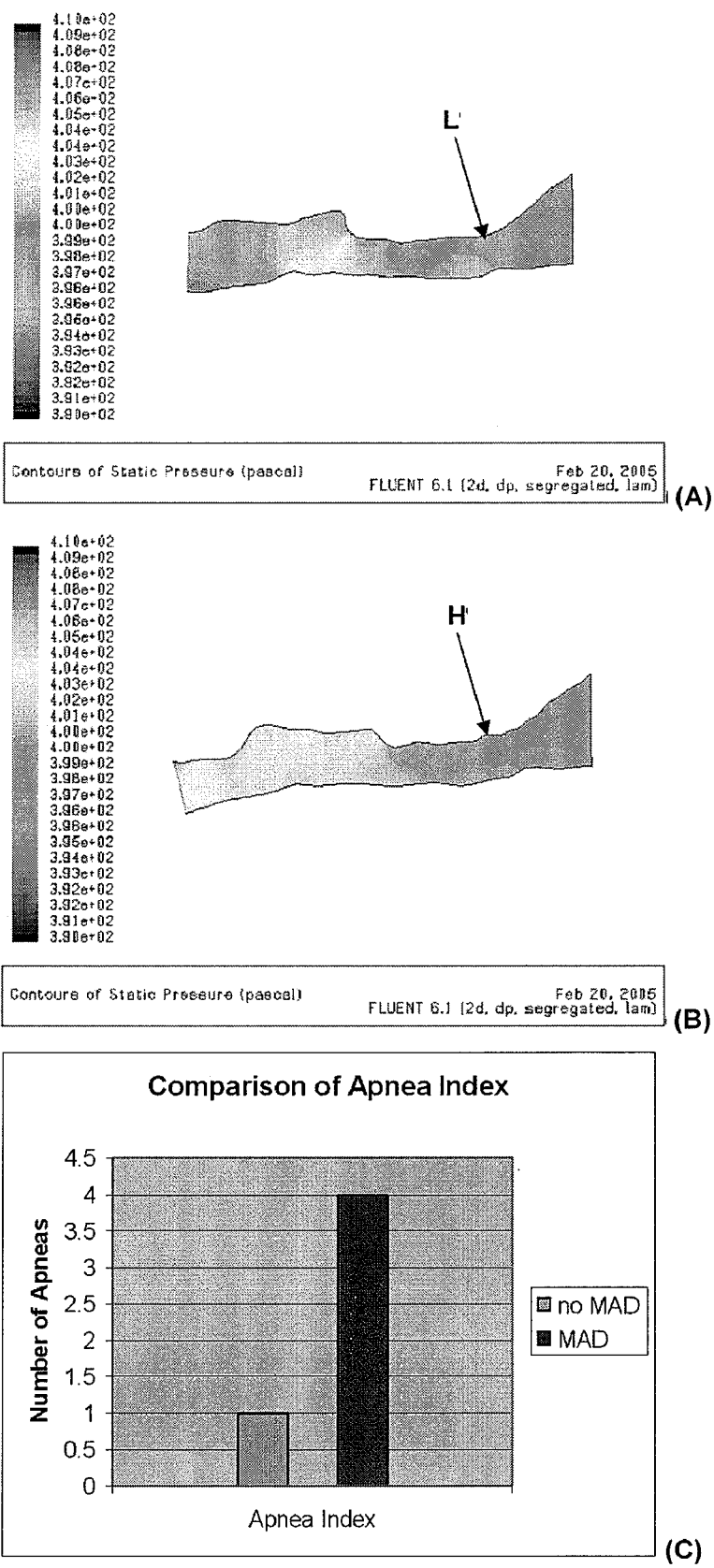
FIG. 35 Pressure contours and apnea index of patient VVM, before and after fitting with MAD.

FIG. 35 shows the CFD models generated by the present invention in patient VVM without a MAD (A) and with a MAD (B). Patient VVM is a 42 year old male, with a BMI of 30. Indicated at position (L) is the narrowest cross-sectional area which is predicted to experience no increase in pressure (H) when the MAD is fitted. For reference, the pressure at point L is in the region of $4.00 \times 10^2$ Pa, remaining at around $4.00 \times 10^2$ Pa (H) in the presence of a MAD. The pressure difference is 0 Pa at expiration peak flow. FIG. 35(C) shows an increase in the AI after fitting (measured by PSG), attributable to an absence of pressure increase at the narrowest cross-sectional area.

It can be seen from the data that for all the cases a decrease in apnea index coincided with a pressure increase at the narrowest cross-sectional area. Patients VDB, JT and VVM showed an improvement in AI using MAD. Patient VVM was not helped with the device, as predicted by the model in that the pressures in the CFD model remained the same and the apnea index even increased. Where occurring, the pressure increase was small and in the same order of magnitude for all cases.

It can be concluded that for patients in whom the Mandibular Advancement Device is effective, a larger initial cross sectional area causes an increase in pressure in the upper airway especially at the end of the expiration, sufficient to improve the condition.

However, it must be noted that even with a MAD, apneas are still predicted to occur. The upper airway model has the potential of comparing different interventions and can assist in deciding the optimal one.

REFERENCES

1. Young, T., M. Palta, J. Dempsey, J. Skatrud, S. Weber, and S. Badr. 1993. The occurrence of sleep-disordered breathing among middle-aged adults. N. Engl. J. Med. 328:1230-1235.

2. De Backer, W. 1998. Non-CPAP treatment of obstructive sleep apnoea. Monaldi Arch. Chest Dis. 53:625-629.

3. Morrell, M. J., Y. Arabi, B. Zahn, and M. S. Badr. 1998. Progressive retropalatal narrowing preceding obstructive apnea. Am. J. Respir. Crit Care Med. 158:1974-1981.

4. Tamisier, R., J. L. Pepin, B. Wuyam, C. Deschaux, and P. Levy. 2004. Expiratory changes in pressure:flow ratio during sleep in patients with sleep-disordered breathing. Sleep 27:240-248.

5. Oostveen, E., D. MacLeod, H. Lorino, R. Farre, Z. Hantos, K. Desager, and F. Marchal. 2003. The forced oscillation technique in clinical practice: methodology, recommendations and future developments. Eur. Respir. J. 22:1026-1041.

6. Levitzky, M. G. 1995. Pulmonary Physiology McGraw-Hill, 33-37.

7. Crystal, R. G. and J. B. West. 1991. The Lung scientific foundations Raven, New York. 995-1009.

8. Fluent Inc 2004. Fluent Manual.

9. Fluent Inc 2004. Fidap Manual.

10. Oliver, R. G. and S. P. Evans. 1986. Tongue size, oral cavity size and speech. Angle Orthod. 56:234-243.

11. Fleetham, J. A. 1992. Upper airway imaging in relation to obstructive sleep apnea. Clin. Chest Med. 13:399-416.

12. Do, K. L., H. Ferreyra, J. F. Healy, and T. M. Davidson. 2000. Does tongue size differ between patients with and without sleep-disordered breathing? Laryngoscope 110:1552-1555.

13. Stafford, C. B. 2004. Update for nurse anesthetists. The Starling resistor: a model for explaining and treating obstructive sleep apnea. AANA. J. 72:133-138.

14. Wuyts, F. L., V. J. Vanhuyse, G. J. Langewouters, W. F. Decraemer, E. R. Raman, and S. Buyle. 1995. Elastic properties of human aortas in relation to age and atherosclerosis: a structural model. Phys. Med. Biol. 40:1577-1597.

15. Isono, S., J. E. Remmers, A. Tanaka, Y. Sho, J. Sato, and T. Nishino. 1997. Anatomy of pharynx in patients with obstructive sleep apnea and in normal subjects. J. Appl. Physiol 82:1319-1326.

16. Isono, S., J. E. Remmers, A. Tanaka, Y. Sho, and T. Nishino. 1996. Static properties of the passive pharynx in sleep apnea. Sleep 19:S175-S177.

17. Gere, J. M. and S. P. Timoshenko. 1999. Mechanics of materials Stanley Thornes, Cheltenham.

18. Caballero, P., R. varez-Sala, F. Garcia-Rio, C. Prados, M. A. Hernan, J. Villamor, and J. L. varez-Sala. 1998. CT in the evaluation of the upper airway in healthy subjects and in patients with obstructive sleep apnea syndrome. Chest 113:111-116.

19. O. M. Vanderveken, E. Oostveen, J. Verbraecken, P. Van de Heyning, and W. A. De Backer. Expiratory Upper Airway Closure Preceding Obstructive Sleep Apnea. submitted. 2004.

Ref Type: Abstract

20. Vanderveken, O. M., A. N. Boudewyns, M. J. Braem, W. Okkerse, J. A. Verbraecken, M. Willemen, F. L. Wuyts, W. A. De Backer, and P. H. Van de Heyning. 2004. Pilot study of a novel mandibular advancement device for the control of snoring. Acta Otolaryngol. 124:628-633.

What is claimed is:

1. A method for determining a treatment of obstructive sleep apnea that lowers the Apnea Index for a subject suffering from the same comprising:
    measuring flow and pressure in the subject at particular locations in the throat to obtain flow and pressure data;
    obtaining a computer-generated structural model of the upper airway of the subject;
    modeling by a computer the air flow through the model of the upper airway of the subject using the flow and pressure data obtained from the subject;
    determining treatments which lead to an increase in flow pressure at the narrowest cross-section thereby reducing the Apnea Index.

2. The method according to claim 1 comprising the step of measuring the flow and pressure at the palatopharynx, oropharynx, and/or hypopharynx of said subject during an apnea episode.

3. The method according to claim 1 comprising the step of obtaining a three-dimensional image of the upper airway of said subject.

4. The method according to claim 3 comprising the step of generating a two dimensional model from said image, comprising a sagittal plane along the central axis of the upper airway.

5. The method according to claim 1 comprising the step of obtaining a two-dimensional image of the upper airway of said subject, comprising a sagittal plane along the central axis of the upper airway.

6. The method according to claim 5 comprising the step of generating a two dimensional model from said image, comprising a sagittal plane along the central axis of the upper airway.

7. The method according to claim 1, wherein the airflow is modeled using a computation fluid dynamic (CFD) code 2 analysis.

8. The method according to claim 7 further comprising determining fluid-structure interactions.

9. The method according to claim 1 comprising implementing a CFD code 1 analysis.

10. A method for the treatment of obstructive sleep apnea in a subject suffering from the same comprising:
    measuring flow and pressure in the subject at particular locations in the throat to obtain flow and pressure data;
    obtaining a model of the upper airway of the subject by magnetic resonance imaging, positron emission tomography or computer tomography;
    modeling the air flow through the upper airway of the subject using the flow and pressure data obtained from the subject;
    determining treatments which lead to an increase in flow pressure at the narrowest cross-section thereby reducing the Apnea Index; and
    administrating at least one of said treatments to the subject, wherein the treatment is selected from a mandibular advancement device (MAD), surgery, or a combination thereof.

11. The method according to claim 10, wherein said treatment comprises providing positive airway pressure.

12. The method according to claim 11, wherein said positive airway pressure is provided at the narrowest cross-section.

13. The method according to claim 11, wherein said positive airway pressure is provided with a mandibular device.

* * * * *

UNITED STATES PATENT AND TRADEMARK OFFICE
CERTIFICATE OF CORRECTION

PATENT NO. : 7,540,843 B2
APPLICATION NO. : 11/576589
DATED : June 2, 2009
INVENTOR(S) : Wilfried De Backer It is certified that error appears in the above-identified patent and that said Letters Patent is hereby corrected as shown below:

Column 1, Line 8, "PCT/EP2004/01108" should be changed to --PCT/EP2004/011108--

Column 3, Line 6, "in y-z plave in" should be changed to --in y-z plane in--

Column 6, Line 62, "a pneumotacograph the" should be changed to --a pneumotachograph the--

Column 7, Line 57, "using Mimcs software" should be changed to --using Mimics software--

Column 10, Line 5, "distributed deformation," should be changed to --distributed deformation.--

Column 16, Line 21, "in pressure:flow ratio" should be changed to --in pressure: flow ratio--

Column 17, Line 16, "air flow through the model of" should be changed to --air flow through--

Column 17, Line 20, "narrowest cross-section" should be changed to --narrowest cross-section,--

Column 18, Line 23, "narrowest cross-section" should be changed to --narrowest cross-section,--

Column 18, Line 25, "administrating at least" should be changed to --administering at least--

UNITED STATES PATENT AND TRADEMARK OFFICE
CERTIFICATE OF CORRECTION

PATENT NO. : 7,540,843 B2
APPLICATION NO. : 11/576589
DATED : June 2, 2009
INVENTOR(S) : Wilfried De Backer It is certified that error appears in the above-identified patent and that said Letters Patent is hereby corrected as shown below:

Column 18, Line 35, "a mandibular device." should be changed to --a mandibular advancement device.--

Signed and Sealed this

Eighth Day of December, 2009

David J. Kappos
*Director of the United States Patent and Trademark Office*